United States Patent
Rubinstein et al.

(10) Patent No.: US 10,377,988 B2
(45) Date of Patent: Aug. 13, 2019

(54) CYTOKINE RECEPTOR GENES AND THE USE THEREOF TO ENHANCE THERAPY

(71) Applicant: MUSC FOUNDATION FOR RESEARCH DEVELOPMENT, Charleston, SC (US)

(72) Inventors: Mark Rubinstein, James Island, SC (US); David Cole, Mount Pleasant, SC (US)

(73) Assignee: MUSC FOUNDATION FOR RESEARCH DEVELOPMENT, Charleston, SC (US)

( * ) Notice: Subject to any disclaimer, the term of this patent is extended or adjusted under 35 U.S.C. 154(b) by 0 days.

(21) Appl. No.: 15/533,103

(22) PCT Filed: Jan. 22, 2016

(86) PCT No.: PCT/US2016/014516
§ 371 (c)(1),
(2) Date: Jun. 5, 2017

(87) PCT Pub. No.: WO2016/118857
PCT Pub. Date: Jul. 28, 2016

(65) Prior Publication Data
US 2018/0057794 A1    Mar. 1, 2018

Related U.S. Application Data

(60) Provisional application No. 62/242,098, filed on Oct. 15, 2015, provisional application No. 62/106,860, filed on Jan. 23, 2015.

(51) Int. Cl.
*C12N 5/0783* (2010.01)
*A61K 35/17* (2015.01)
*A61K 38/17* (2006.01)
*A61K 38/20* (2006.01)
*C07K 14/715* (2006.01)
*C12N 15/85* (2006.01)
*C07K 14/705* (2006.01)

(52) U.S. Cl.
CPC ............ *C12N 5/0638* (2013.01); *A61K 35/17* (2013.01); *A61K 38/1793* (2013.01); *A61K 38/20* (2013.01); *A61K 38/2013* (2013.01); *C07K 14/705* (2013.01); *C07K 14/70521* (2013.01); *C07K 14/715* (2013.01); *C07K 14/7155* (2013.01); *C12N 15/85* (2013.01); *C12N 2510/00* (2013.01)

(58) Field of Classification Search
None
See application file for complete search history.

(56) References Cited

U.S. PATENT DOCUMENTS

| | | |
|---|---|---|
| 5,352,772 A | 10/1994 | Smith |
| 9,629,877 B2 | 4/2017 | Cooper et al. |
| 2012/0093842 A1 | 4/2012 | Eshhar et al. |
| 2014/0286987 A1 | 9/2014 | Spencer et al. |

FOREIGN PATENT DOCUMENTS

WO    WO 2015/123527    8/2015

OTHER PUBLICATIONS

Kuhn, et al. (2003) "Overexpression Interleukin-2 Receptor a in a Human Squamous Cell Carcinoma of the Head and Neck Cell Line Is Associated With Increased Proliferation, Drug Resistance, and Transforming Ability", Journal of Cellular Biochemistry, 89: 824-36. (Year: 2003).*
Shaikh, et al. (2006) "Optimization of the Tet-On System for Inducible Expression of RAGE", Journal of Biomolecular Techniques, 17: 283-92 (Year: 2006).*
Wilde, et al. (2014) "Abnormal Expression Pattern of the IL-2 Receptor β-Chain on CD4+ T cells in ANCA-Associated Vasculitis", Disease Markers, vol. 2014, Article ID 249846, 9 pages long. (Year: 2014).*
Chmielewski, et al. (2013) "Antigen-Specific T-Cell Activation Independently of the MHC: Chimeric Antigen Receptor-Redirected T Cells", Frontiers in Immunology, 4: Article 371, 7 pages. (Year: 2013).*
Perna, et al. (Jan. 3, 2014) "Genetic modification of cytotoxic T lymphocytes to express cytokine receptors" In: Lawman M., Lawman P. (Eds) Cancer Vaccines. Methods in Molecular Biology (Methods and Protocols), vol. 1139: Humana Press, New York, NY. (Year: 2014), pp. 189-200. Printed as HTML, 21pgs.*
Su, et al. (2015) "IIL-2Rα mediates temporal regulation of IL-2 signaling and enhances immunotherapy", Science Translational Medicine, 7(311): article 311ra170, pp. 1-9.*
Amano et al., "A hydrophobic amino acid cluster inserted into the C-terminus of a recycling cell surface receptor functions as an endosomal sorting signal," *BBRC*, 441:164-168, 2013.
Bacha et al., "Interleukin 2 receptor-targeted cytotoxicity. Interleukin 2 receptor-mediated action of a diphtheria toxin-related interleukin 2 fusion protein," *J. Exp. Med.*, 167(2):612-622, 1988.

(Continued)

*Primary Examiner* — Robert M Kelly

(74) *Attorney, Agent, or Firm* — Parker Highlander PLLC

(57) ABSTRACT

Cells, such a T-cells, are provided that comprise cytokine receptors having increased activity in response to their ligand. For example, cell can comprise IL-2 and/or IL-15 receptors having increased surface expression or signaling activity. Cells of the embodiments have a significant growth advantage in the presence of cytokines and can be used, e.g., for enhanced adoptive cell transfer therapies.

9 Claims, 29 Drawing Sheets

Specification includes a Sequence Listing.

(56) References Cited

OTHER PUBLICATIONS

Boyman et al., "Selective Stimulation of T Cell Subsets with Antibody-Cytokine Immune Complexes," *Science*, 311:1924-1927, 2006.
PCT International Invitation to Pay Additional Fees issued in International Application No. PCT/US2016/014516, dated Apr. 22, 2016.
PCT International Search Report and Written Opinion issued in International Application No. PCT/US2016/014516, dated Jul. 1, 2016.
Rubinstein et al., "Converting IL-15 to a superagonist by binding to soluble IL-15R{alpha}," *Proc. Natl. Acad. Sci. U. S. A.*, 103(24):9166-71, 2006.
Rubinstein et al., "Ex vivo interleukin-12-priming during CD8(+) T cell activation dramatically improves adoptive T cell transfer anti-tumor efficacy in a lymphodepleted host," *Journal of the American College of Surgeons*, 214, 700-707; discussion 707-708, 2012.
Shin et al., "Epigenetic Modifications Induced by Blimp-1 Regulate CD8+ T Cell Memory Progression during Acute Virus Infection," *Immunity*, 39:661-675, 2013.
Teege et al., "Tuning IL-2 signaling by ADP-ribosylation of CD25," *Scientific reports*, 5:8959, 2015.
Gasser et al., "Constitutive expression of a chimeric receptor that delivers IL-2/IL-15 signals allows antigen-independent proliferation of CD8+CD44high but not other T cells," *Journal of Immunology*, 164(11):5659-5667, 2000.
Gesbert et al., "IL-2 responsiveness of CD4 and CD8 lymphocytes: further investigations with human IL-2Rbeta transgenic mice," *International Immunology*, 17(8):1093-1102, 2005.
Kondo et al., "Expression of functional human interleukin-2 receptor in mouse T cells by cDNA transfection," *Nature*, 320(6057):75-77, 1986.
Medveczky et al., "Expression of interleukin 2 receptors in T cells transformed by strains of Herpesvirus saimiri representing three DNA subgroups," *Intervirology*, 30(4):213-226, 1989.
Melenhorst et al., "Innovation and opportunity for chimeric antigen receptor targeted T cells," *Cytotherapy*, 15(9):1046-1053, 2013.
Soldaini et al., "Mouse interleukin-2 receptor alpha gene expression. Delimitation of cis-acting regulatory elements in transgenic mice and by mapping of DNase-I hypersensitive sites," *Journal of Biological Chemistry*, 270(18):10733-10742, 1995.
Su et al., "IL-2Rα mediates temporal regulation of IL-signaling and enhances immunotherapy," *Science Translational Medicine*, 7(311):1-9, 2015.
Sugamura, "Expression of IL-2 Receptor Subunits, α, β, and γ, on HTLV-I-Transformed T Cells," *Gann Monographs on Cancer Research*, 39:119-128, 1992.
Supplementary Partial European Search Report issued in European Patent Application No. 16740831.9, dated Aug. 18, 2018.

* cited by examiner

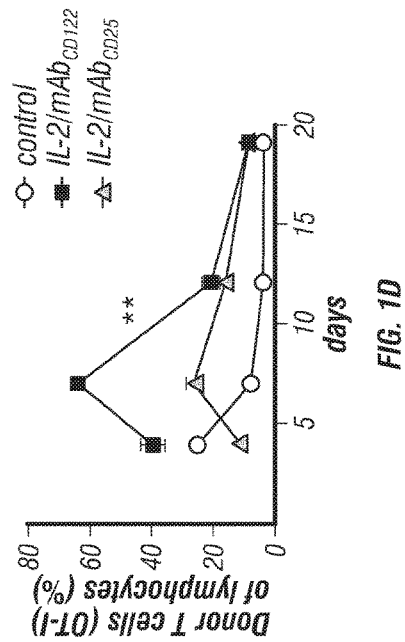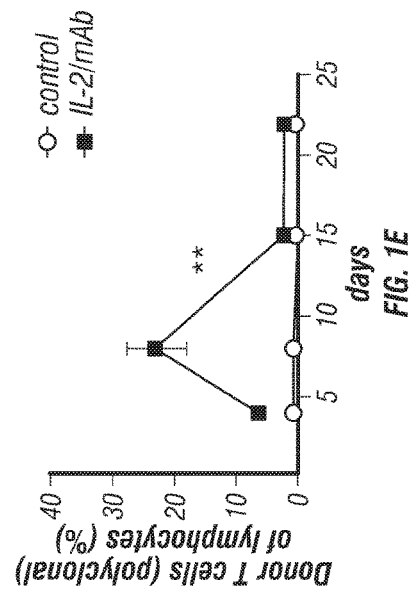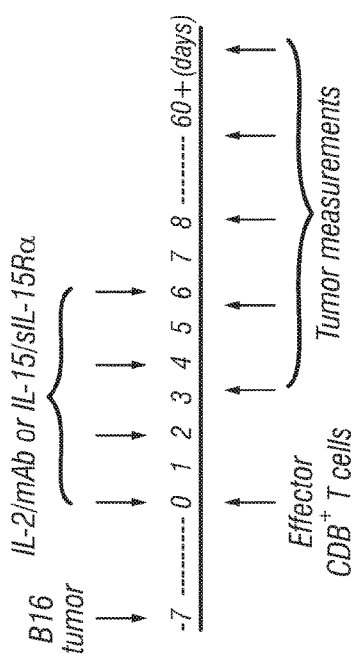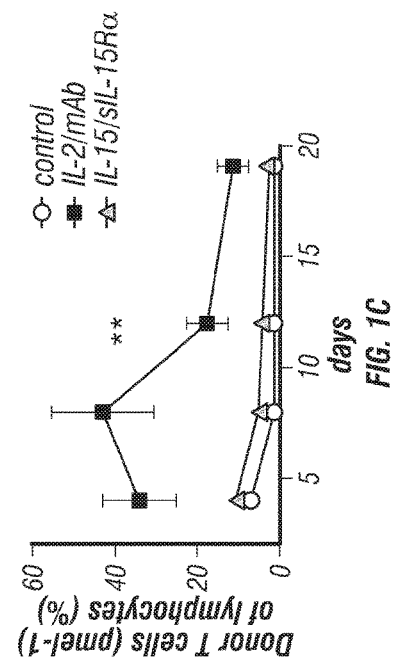
FIG. 1A
FIG. 1C
FIG. 1D
FIG. 1E

*Pulse/wash assay*

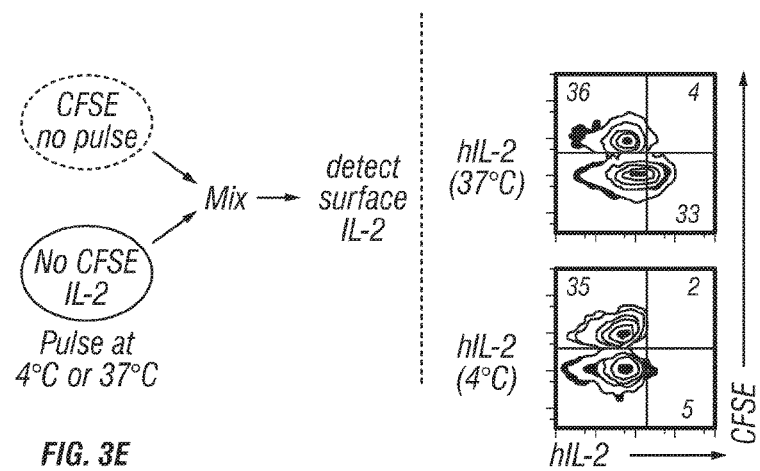
FIG. 3E
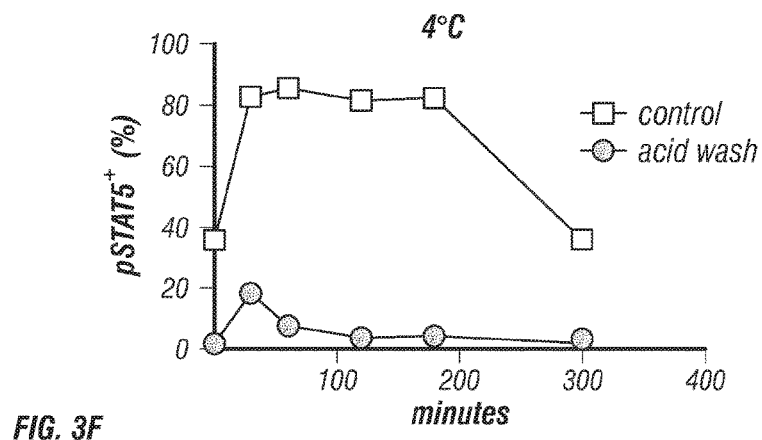
FIG. 3F
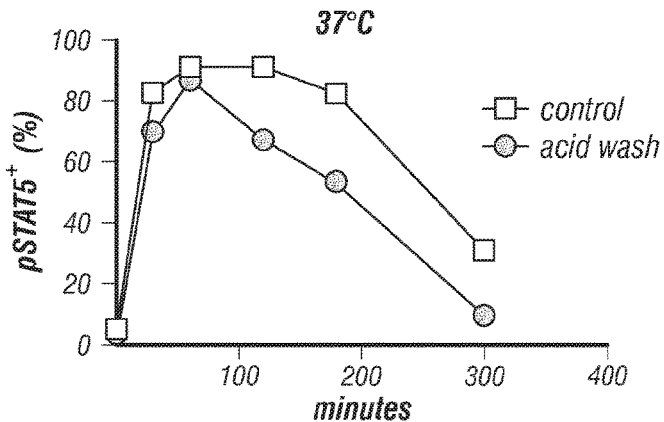

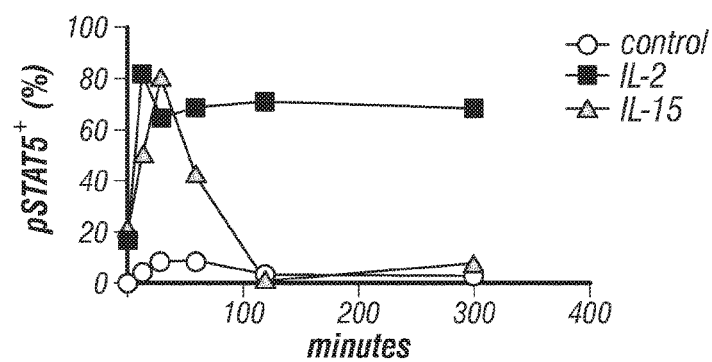
FIG. 15A
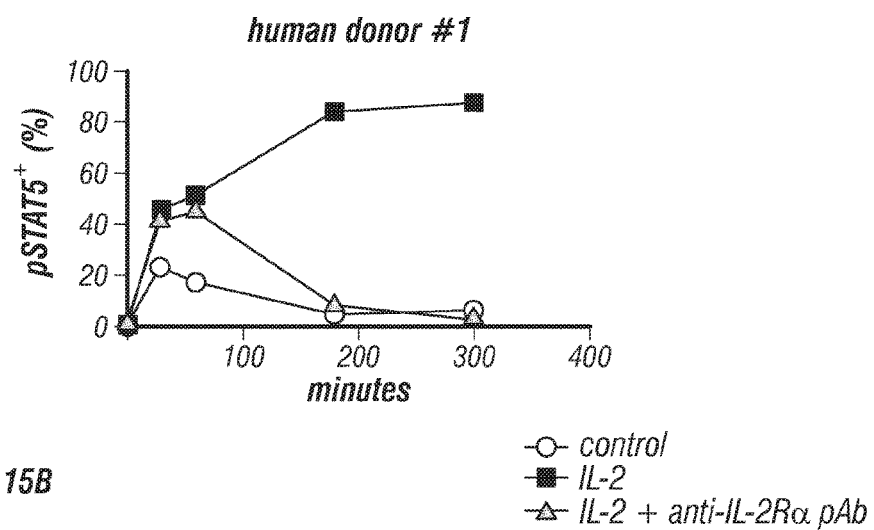
FIG. 15B
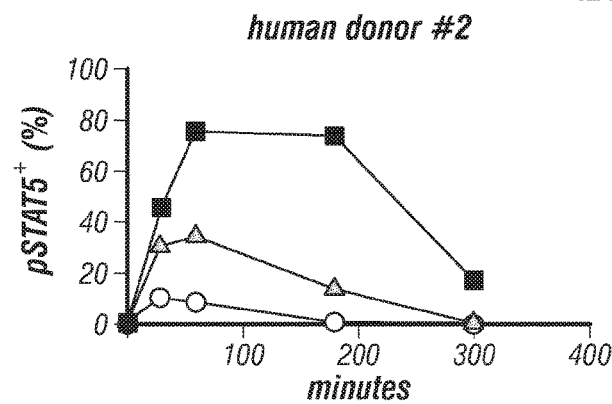

ical biology, immunology and medicine. In particular,
CYTOKINE RECEPTOR GENES AND THE USE THEREOF TO ENHANCE THERAPY This application is a national phase application under 35 U.S.C. § 371 of International Application No. PCT/US2016/014516, filed Jan. 22, 2016, which claims the benefit of U.S. Provisional Patent Application No. 62/106,860, filed Jan. 23, 2015 and 62/242,098, filed Oct. 15, 2015, the entirety of each are incorporated herein by reference.

Pursuant to 37 C.F.R. 1.821(c), a sequence listing is submitted herewith as an ASCII compliant text file named "MESCP0094US$_{13}$ ST25.txt", created on May 2, 2017 and having a size of ~1 kilobytes. The content of the aforementioned file is hereby incorporated by reference in its entirety.

GOVERNMENT SUPPORT CLAUSE

The invention was made with government support under Grant No. P01CA54778-01 awarded by the National Institutes of Health. The government has certain rights in the invention.

BACKGROUND OF THE INVENTION

1. Field of the Invention

The present invention relates generally to the fields of molecular biology, immunology and medicine. In particular, embodiments of the invention relate to transferring of cytokine receptor genes or modulation of cytokine receptor gene expression to enhance sensitivity to cytokine therapy.

2. Description of Related Art

Recently, there has been increasing interest in cell-based therapies to treat disease. For example, therapies using T-cells targeted to tumor antigens, such as chimeric antigen receptor T-cells, are being studied as potential new anti-cancer therapies. However, for such therapies to be effective, the therapeutic cells must be able to proliferate in vivo. Accordingly, many of these therapies rely upon administration of exogenous cytokines, such as IL-2, to the patients being treated. The administration of IL-2 and many other cytokines/protein therapeutics is often limited by dose limiting toxicity. In the case of IL-2, for example, therapeutic effector cells may respond inefficiently to the cytokine. Thus, there remains a need for therapeutic cells with enhanced proliferative capability or enhanced response to cytokines.

SUMMARY OF THE INVENTION

In a first embodiment there is provided an isolated cell comprising (i) an elevated surface expression level of at least one cytokine receptor or cytokine receptor co-stimulator (e.g., relative to an activated or naïve T-cell); or (ii) a nucleic acid molecule encoding at least one cytokine receptor or cytokine receptor co-stimulator polypeptide comprising a mutation that increases the activity of the receptor. For example, the at least one cytokine receptor can be selected from IL-2R (a receptor for IL-2), IL-15R (a receptor for IL-15), IL-12R (a receptor for IL-12), IL-6R (a receptor for IL-6), GP130 (a receptor for IL-6, IL-35 or IL-27), IL-4R (a receptor for IL-4), IL-2Rγ (a receptor for IL-4 or IL-9), IL-27R (a receptor for IL-27), IL-2Rβ2 (a receptor for IL-35), IL-12Rβ1 (a receptor for IL-23), IL-23R (a receptor for IL-23), IL-9R (a receptor for IL-9), G-CSFR (a receptor for G-CSF and the neupogen or neulasta ligands) or GM-CSF (a receptor for GM-CSF). In a further aspects, the cytokine receptor co-stimulator is ICOS (which binds to ICOS ligand), 4-1BB (which binds to 4-1BB ligand) or CD28 (which binds to B7-1 or B7-2). In some aspects, the cell is a mammalian cell, such as a human cell. In further aspects, the cell is an immune cell, such as a T-cell, Natural Killer (NK) cell or NK T-cell. In specific aspects, the T-cell is a cytotoxic T-cell, an inflammatory T-cell, an effector T-cell or a memory T-cell. In further aspects, the T-cell is a CD4$^+$ or CD8$^+$ T-cell. In further aspects, the T cell is an alpha/beta T cell, a gamma/delta T cell, NK T cell, or other lymphocyte subpopulation. In still further aspects, the cell is comprised in a bone marrow graft cell population.

Thus, in a further embodiment there is provided an isolated transgenic cell comprising (i) an elevated surface expression level of a cytokine receptor; or (ii) a nucleic acid molecule encoding a cytokine receptor polypeptide comprising a mutation that increases the activity of the receptor (e.g., when bound to the cytokine ligand). For example, in some aspects, the cytokine receptor is proliferative cytokine receptor, such as an IL-2 receptor (e.g., IL-2Rα), GM-CSF receptor (e.g., GM-CSFRα or GM-CSFRβc), G-CSF receptor, IL-12 receptor (e.g., IL-12Rβ1 or IL-12Rβ2) or an IL-15 receptor (e.g., IL-15Rα).

In further embodiment there is provided an isolated transgenic cell, such as a T-cell, comprising (i) an elevated surface expression level of an IL-2 receptor; or (ii) a nucleic acid molecule encoding an IL-2 receptor polypeptide comprising a mutation that increases the activity of the receptor. For example, the elevated surface expression level of an IL-2 receptor, can be elevated relative to the expression level exhibited by an activated T-cell. In further aspects of the invention, expression will be elevated versus a naïve or unactivated T cells. In still further aspects, a cell of the embodiments may comprise IL-2R expression that is maintained in culture conditions that would normally down regulate IL-2R. In certain aspects, an IL-2 receptor polypeptide of the embodiments is an IL-2Rα, IL-2Rβ and/or IL-2Rγ polypeptide.

Thus, in specific aspects, an isolated cell of the embodiments comprises a nucleic acid molecule encoding an IL-2 receptor polypeptide comprising a mutation that increases the activity of the receptor. In particular aspects, the IL-2 receptor is IL-2Rα (also referred to as CD25). In other aspects, the IL-2 receptor is IL-2Rβ (also referred to as CD122) or IL-2Rγ (also referred to as CD132). In some aspects, the mutation increase surface expression, increases stability or increases ligand binding of the IL-2 receptor polypeptide. In certain aspects, the mutation disrupts one or more ribosylation sites on IL2-Rα (see, e.g., Teege et al., 2015, incorporated herein by reference). In further aspects, the signal sequence for recycling and/or endosomal sorting of the IL-2 receptor is modified to alter the natural distribution or re-expression of the receptor (see, e.g., Amano et al., 2013, incorporated herein by reference). In still further aspects, a nucleic acid molecule encoding the IL-2 receptor polypeptide is operably linked to a heterologous promoter. In certain aspects, the heterologous promoter is a ligand inducible or a ligand repressible promoter. In some aspects, the ligand inducible promoter is a tet-on promoter. In certain aspects, the nucleic acid molecule encoding the IL-2 receptor polypeptide is integrated into the genome of the cell or is encoded on an episomal vector. In further specific aspects, the nucleic acid molecule encoding the IL-2 receptor polypeptide is flanked by retroviral long terminal repeats or transposon repeats.

In a further embodiment there is provided an isolated transgenic cell, such as a T-cell, comprising (i) an elevated surface expression level of an IL-15 receptor; or (ii) a nucleic acid molecule encoding an IL-15 receptor polypeptide comprising a mutation that increases the activity of the receptor. For example, the elevated surface expression level of an IL-15 receptor, can be elevated relative to the expression level exhibited by an activated T-cell. In further aspects of the invention, expression will be elevated versus a naïve or unactivated T cells. In still further aspects, a cell of the embodiments may comprise IL-15R expression that is maintained in culture conditions that would normally down regulate IL-15R. In certain aspects, an IL-15 receptor polypeptide of the embodiments is an IL-15Rα, IL-2Rβ and/or IL-2Rγ polypeptide.

Thus, in specific aspects, an isolated cell of the embodiments comprises a nucleic acid molecule encoding an IL-15 receptor polypeptide comprising a mutation that increases the activity of the receptor. In particular aspects, the IL-15 receptor is IL-15Rα. In other aspects, the IL-15 receptor is IL-2Rβ or IL-2Rγ. In some aspects, the mutation increase surface expression, increases stability or increases ligand binding of the IL-15 receptor polypeptide. In further aspects, the signal sequence for recycling and/or endosomal sorting of the IL-15 receptor is modified to alter the natural distribution or re-expression of the receptor (see, e.g., Amano et al., 2013, incorporated herein by reference). In still further aspects, a nucleic acid molecule encoding the IL-15 receptor polypeptide is operably linked to a heterologous promoter. In certain aspects, the heterologous promoter is a ligand inducible or a ligand repressible promoter. In some aspects, the ligand inducible promoter is a tet-on promoter. In certain aspects, the nucleic acid molecule encoding the IL-15 receptor polypeptide is integrated into the genome of the cell or is encoded on an episomal vector. In further specific aspects, the nucleic acid molecule encoding the IL-15 receptor polypeptide is flanked by retroviral long terminal repeats or transposon repeats.

In yet still a further aspect of the above embodiments, an isolated cell comprises a further transgene, such as a suicide gene, a chimeric antigen receptor (CAR) or a recombinant T-cell receptor (TCR). Such a further transgene may be encoded on the same nucleic acid molecule as a cytokine receptor of the embodiments or may be encoded on a separate molecule. In some aspects, the further transgene is a suicide gene that is operably linked to an inducible promoter. For example, the suicide gene can be a thymidine kinase gene. In further aspects a cell of the embodiments comprises a cell surface marker. For example, the cell can comprise a marker such as CD20 that can be depleted by antibody administration.

In some aspects, an isolated cell of the embodiments is a T-cell or an NK-cell targeted to an infectious disease or cancer cell antigen. For example, the cancer cell antigen can be an oncogene or a growth factor receptor. In particular aspects, the cancer cell antigen is CD19, CD20, GP240, 5T4, HER1, CD-33, CD-38, VEGFR-1, VEGFR-2, CEA, FGFR3, IGFBP2, IGF-1R, BAFF-R, TACI, APRIL, Fn14, EGFR, ERBB2, ERBB3 or mesothelin. In further aspects, the isolated cell expresses a chimeric antigen receptor (CAR) or a recombinant T-cell receptor (TCR) targeted to an infectious disease or cancer cell antigen.

In a further embodiment there is provided a pharmaceutical composition comprising an isolated cell in accordance with any of the embodiments and aspects described above in a pharmaceutically acceptable carrier. In some aspects, the composition comprises between about $1\times10^3$ and $1\times10^4$, $1\times10^5$, $1\times10^6$, $1\times10^7$, $1\times10^8$, $1\times10^9$, $1\times10^{10}$, $1\times10^{11}$ or $1\times10^{12}$ cells in accordance with any of the embodiments and aspects described above.

In still a further embodiment, there is provided a method of providing a T-cell response in a human subject having a disease comprising administering an effective amount of T-cells having increased expression or activity of a cytokine receptor, as described above, to the subject. In certain aspects, the T-cell response is a regulatory T-cell response. In other aspects, the T-cell response is a cytotoxic T-cell response. In further aspects, the method further comprises administering a cytokine that stimulates T-cell proliferation to the subject. In particular aspects, the cytokine is IL-2 or IL-15. In some aspects, the cytokine administered to the subject (e.g., IL-2 or IL-15) comprises a mutation that increases receptor binding. In some aspects, the cytokine has been modified to increase serum half-life. For example, the cytokine can be PEGylated or fused to an Fc polypeptide. In a further aspect, the cytokine may be bound to an antibody or soluble receptor. For example, IL-2 may be bound to anti-IL-2 mAb or IL-15 may be bound to soluble IL-15Rα with or without an Fc fusion (see, e.g., Boyman et al., 2006 and Rubinstein et al., 2006, each of which are incorporated herein by reference).

In yet a further embodiment there is provided a method for controlling a T-cell response in a subject. In some aspects, such a method comprises identifying a subject who has been treated with a cell population of the embodiments (e.g., cells comprising increased cytokine receptor activity, such as increased IL-2R activity) and administering a therapeutic the subject that selectively kills or inhibits proliferation of the cell population. For example, in the case of a cell population having increased IL-2R activity, a subject can be administered an IL-2-like molecule that is fused or conjugated to a toxin (such as ricin or gelonin). In some aspects, the IL-2-like molecule preferentially binds cells with elevated IL-2Rα expression and leads to their destruction or depletion. In further aspects, a subject can be administered an antibody to the cytokine receptor having increased activity. For example, a subject can be administered an antibody against IL-2Rα (or other receptor subunit protein) to deplete or destroy cells that are no longer desirable. For instance, the antibody could be daclizumab (anti-IL-2Rα mAb).

In yet still a further embodiment, there is provided a method of producing therapeutic cells comprising: (i) selecting a population of cells having increased cytokine receptor activity (or cytokine co-receptor activity), for a proliferative cytokine receptor; and (ii) culturing the cells in the presence of a ligand for the proliferative cytokine receptor. In further aspects, the method may further comprise (i) selecting a population of cells having increased cytokine receptor activity (or cytokine co-receptor activity), for a proliferative cytokine receptor; (ii) culturing the cells in the presence of a ligand for the proliferative cytokine receptor, thereby producing an expanded call population; and (iii) selecting cells from the expanded population that do not have increased cytokine receptor activity. For example, an expanded cell population can be treated with and agent that reduces the activity of expression level of the cytokine receptor. In a further aspect, the method comprises (i) selecting a population of cells having increased IL-2 or IL-15 receptor activity; and (ii) culturing the cells in the presence of IL-2 or IL-15. In certain aspects, the cells having increased IL-2 or IL-15 receptor activity express or an elevated level of surface IL-2 or IL-15 receptor on their surface. In further aspects, selecting a population of cells having increased IL-2 or IL-15 receptor activity comprises contacting the cells a drug that increases IL-2 or IL-15 receptor expression. In certain aspects, selecting a population of cells having increased IL-2 or IL-15 receptor activity comprises sorting cells based on IL-2 or IL-15 receptor expression. In some particular aspects, the cells comprise a nucleic acid molecule encoding an IL-2 or IL-15 receptor polypeptide comprising a mutation that increases the activity of the receptor.

In a further embodiment, there is provided a method of producing cells with elevated receptor or receptor subunit expression (e.g., using methods not requiring the transfer of genetic material). For example, therapeutic cells can be cultured with pharmacological agents before adoptive transfer and/or the pharmacological agents can be administered during or after adoptive transfer. For example, the pharmacological agents can include, without limitation, cytokines, agonists for co-stimulatory molecules, epigenetic drugs, or related compounds. Thus, therapeutic cells can be cultured in a cytokine such as IL-12 and/or IL-18 before adoptive transfer. For example, the therapeutic cells can be cultured in a cytokine such as IL-21 before adoptive transfer. In further aspects, the therapeutic cells are cultured with an agonist against co-stimulatory molecules such as CD28, ICOS, or 4-1BB. In yet further aspects, the therapeutic cells are cultured with epigenetic drugs that target certain pathways, such as HDAC2 and G9a which repress expression of IL-2Ra (see, e.g., Shin et al., 2013, which is incorporated herein by reference).

In yet a further embodiment, there is provided a method of producing cells with elevated receptor or receptor subunit expression (e.g., using methods not requiring the transfer of genetic material) comprising sorting or enriching cells for a receptor or a receptor subunit expression prior to culture, during culture, or immediately prior to adoptive transfer. For example, cell can be sorted or selected using an antibody against IL-2Rα (e.g., by fluorescence assisted cell sorting (FACS), column purification or bead sorting of cells expressing elevated levels of IL-2Rα). Such sorted cells may be cultured for an additional period of time or immediately adoptively transferred. This method can optionally be used with cell and methods of the embodiments described herein above. In some aspects, this methodology has the added benefit of allowing the receptor to be used as selectable marker to enrich or isolate genetically modified T cells.

In still a further embodiment there is provided a method of treating a disease comprising transferring at least one receptor gene into at least one cell and treating said cell or cells with an agonist of the receptor transcribed by said receptor gene. In some aspects, the receptor gene is a cytokine receptor gene. In specific aspects, the cytokine receptor gene is Interleukin-2 receptor α (IL-2Rα). In particular aspects, the agonist is Interleukin-2 (IL-2). In certain aspects, the disease is cancer. In further aspects, the receptor gene is transferred into the at least one cell via adoptive cell therapy. In some aspects, the treatment does not require lymphodepletion. In other aspects, the at least one cell is a donor T cell. In certain aspects, a treatment method of the embodiments may require lower amounts of lymphodepletion relative to currently used clinical protocols for adoptive cell transfer. Furthermore, in some aspects, treatment methods of the embodiments can comprise low dose administration of a cytokine ligand (following adoptive transfer of cells). In particular, because cells of the embodiments have increased activity of a cytokine receptor (e.g., IL-2R), lower doses of the receptor ligand (e.g., IL-2) are effective to provide stimulation of the transferred cells.

In an additional embodiment, there is provided a method to expand specific populations of cells in vivo. In some aspects, patients may be directly injected with a vector (e.g., a retroviral vector) encoding a CAR linked to an IL-2Rα. Following injection, the patient is administered a IL-2-based therapy and the cells transduced with this vector will preferentially expand. Vectors for use according to the embodiments include, without limitation, a retroviral vector, a lentiviral vector, adenoviral vector, an adeno-associated viral vector or a plasmid vector (e.g., delivered by a gene gun or liposome delivery system). In some cases, the responding cells would be only genetically modified for a short period of time and in other cases the cells would be permanently genetically modified. For example, the vector encoding the CAR and/or cytokine receptor can be an episomal vector or a mRNA vector.

In a further embodiment there is provided a method for providing an enhanced immune response in a subject. For example, an immunogenic composition can be administered to a subject in conjunction with a pharmacological agents to improve receptor or receptor subunit expression or activity (e.g., to enhance IL-2R or IL-2Rα expression or activity). For instance, following immunization with an antigen the mammalian subject can be given pharmacological agent to improve receptor or receptor subunit expression. Examples of pharmacological agents according to this embodiment include, without limitation, epigenetic drugs targeting HDAC2 or G9a that improve the durability of IL-2Ra expression. In further aspects, a subject can be administered an IL-2-based therapy that will selectively expand those cells responding to vaccination and with elevated IL-2Ra.

Aspects of the invention provide that genetically transferring cytokine receptor genes, such as the high affinity IL-2Rα, into lymphocytes or other cells, will dramatically enhance sensitivity to cytokine therapy. There are multiple advantages to this approach: 1) It will not be necessary to give high amounts of IL-2, which is associated with life threatening toxicity, as adoptively transferred cells will respond to a much lower dose of IL-2; 2) It may be possible to make cells IL-2 responsive that are not IL-2 responsive; 3) Genetic modification of donor T cells with IL-2Rα allows for effective adoptive cellular therapy strategies in a lymphoreplete environment. Lymphodepletion, which, although highly toxic, is often required by patients undergoing adoptive cellular therapy in order to allow donor cells to efficiently engraft (FIG. 21c). This is thought to be due to the ability of lymphodepletion to increase the levels of endogenous cytokines. By eliminating lymphodepletion, patients may remain eligible for other types of therapies, such as checkpoint inhibition therapy.

Aspects of the embodiments refer to cytokine receptor activity. As used herein receptor activity refers to signaling from a receptor when bound to the receptor ligand. Thus, a cell having increased receptor activity can have, for example, increased receptor expression, increased receptor expression at the cell surface, increased affinity of the receptor for its ligand (e.g., the ability of the receptor to bind to and/or release ligand), increased receptor stability or increased receptor half-life, all of which increase the signaling activity of the receptor in the presence of ligand.

Aspects, of the embodiments also refer to receptor genes. As used herein the term receptor gene encompasses genes of all subunits of a particular receptor (e.g., the IL-2R α, β and γ subunits).

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%. Most preferred is a composition in which no amount of the specified component can be detected with standard analytical methods.

As used herein in the specification and claims, "a" or "an" may mean one or more. As used herein in the specification and claims, when used in conjunction with the word "comprising", the words "a" or "an" may mean one or more than one. As used herein, in the specification and claim, "another" or "a further" may mean at least a second or more.

As used herein in the specification and claims, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating certain embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1a-1e—IL-2/mAb but not IL-15/sIL-15Rα complexes induce potent effector T cell responses in tumor-bearing mice. (a) Treatment scheme for B6 mice injected s.c. with B16 melanoma tumor cells 7 days prior to the adoptive transfer of $3 \times 10^6$ pmel-1 Tc1 cells. Mice were then treated with hIL-2/mAb (clone 5355) or hIL-15/sIL-15Rα complexes. (b) Tumor volume from 'a' (n=9/group); each line represents one mouse. (*) Based on a log-rank test and time to sacrifice (at 400 mm$^2$) for analysis, mice treated with IL-2/mAb complexes had significantly improved outcomes versus each other condition (p<0.001 for each comparison). The average tumor areas when treatment was initiated ranged between 15-20 mm$^2$ between the 4 groups. (c) The frequency of donor Tc1 cells in the blood of mice (n=4/group) treated as in 'a' but in the absence of tumor. Each point represents the average and bars indicate standard error. (d) The frequency of donor OT-I Tc1 cells in the blood of mice (n=5/group) treated with mIL-2/mAb$_{CD122}$ (clone S4B6) or mIL-2/mAb$_{CD25}$ (clone 1A12). Each point represents the average and bars indicate standard error. (e) The frequency of donor polyclonal T cells in the blood of mice (n=5/group) treated with hIL-2/mAb (clone 5355) complexes or vehicle alone. Each point represents the average and bars indicate standard error. For c-e, (**) indicates a significant difference (p<0.001) between indicated and other conditions. Random effects linear regression was used for modeling data and calculating p-values comparing conditions. All results are representative of at least 2 independent experiments.

FIGS. 3a-3g—IL-2Rα facilitates sustained IL-2 signaling through creation of an extracellular reservoir and recycling. (a) Presence of IL-2 on the surface of polyclonal T cells depends on IL-2Rα. Polyclonal effector CD8$^+$ T cells were pulsed for 2 hours with or without mIL-2. Prior to (and during) the pulse, T cells were incubated with anti-IL-2Rα mAb (PC61). Cells were then washed and stained for surface IL-2. (b) Time course of surface IL-2 on polyclonal T cells after reculture at 37° C. (c) Levels of pSTAT5 in Tc1 cells that were pulsed with IL-2, washed, and recultured at 37° C. with or without anti-IL-2 mAb (clone S4B6 or 1A12). (d) Recycling of IL-2 on effector T cells. Pmel-1 Tc1 cells were incubated with hIL-2 or mIL-2 at 37° C. for 2 hours. As indicated, cells were then acid washed and recultured at 37° C. for 90 minutes in the presence of anti-hIL-2 mAb conjugated to Alexa647. Cells were then washed, fixed, and assayed by flow cytometry. (e) Recycling of IL-2 on pulsed cells while mixed with non-pulsed cells. Pmel-1 Tc1 cells were pulsed with hIL-2 at either 4° C. or 37° C. for 2 hours, and then acid washed. Cells were then mixed with non-pulsed CFSE-labeled Tc1 cells. The mixed cells were recultured at 37° C. for 45 minutes in the presence of anti-hIL-2 mAb conjugated to Alexa647. Cells were then washed, fixed, and assayed by flow cytometry. (f) Internalized IL-2 leads to sustained pSTAT5 signaling. Pmel-1 Tc1 cells were pulsed with hIL-2 at either 4° C. or 37° C. for 2 hours, and then acid washed. Cells were then recultured at 37° C. and assayed for pSTAT5. (g). Subcellular localization of hIL-2 and IL-2Rα (upper panel). Pmel-1 Tc1 cells were pulsed with hIL-2 (or media alone) for 1 hour at 37° C., and stained for hIL-2 and IL-2Rα. Cells were then imaged by confocal microscopy. Subcellular localization of hIL-2 and Rab5 (lower panel). As described for the upper panel, except cells were stained for Rab5. Results are representative of 3 independent experiments.

FIGS. 15a-15b—Human effector $CD8_+$ T cells pulsed with IL-2 mediate sustained IL-2Rα-dependent signaling. (a) Human PBMCs activated with plate-bound anti-CD3 mAb for 3 days were pulsed with either hIL-2 or hIL-15 at 37° C. for one hour. Effector cells were then washed to remove unbound cytokine and recultured in media without cytokine at 37° C. At the indicated times, cells were fixed and stained for CD8 and pSTAT5. The percentage indicates the frequency of $CD8_+$ T cells staining positive for pSTAT5. (b) Human PBMCs from two healthy adult donors were activated for 2 days with plate-bound anti-CD3 mAb. Effector cells were then pulsed with hIL-2 in the absence or presence of an anti-IL-2Rα pAb (R&D systems, AB-223-NA) for two hours. pSTAT5 was assessed in these cells at the indicated times in a manner similar to 'a'. For 'a & b', similar results were obtained with $CD8_+$ T cells derived from 4 healthy adult donors.

DESCRIPTION OF ILLUSTRATIVE EMBODIMENTS

I. The Present Embodiments

Figure 1B:
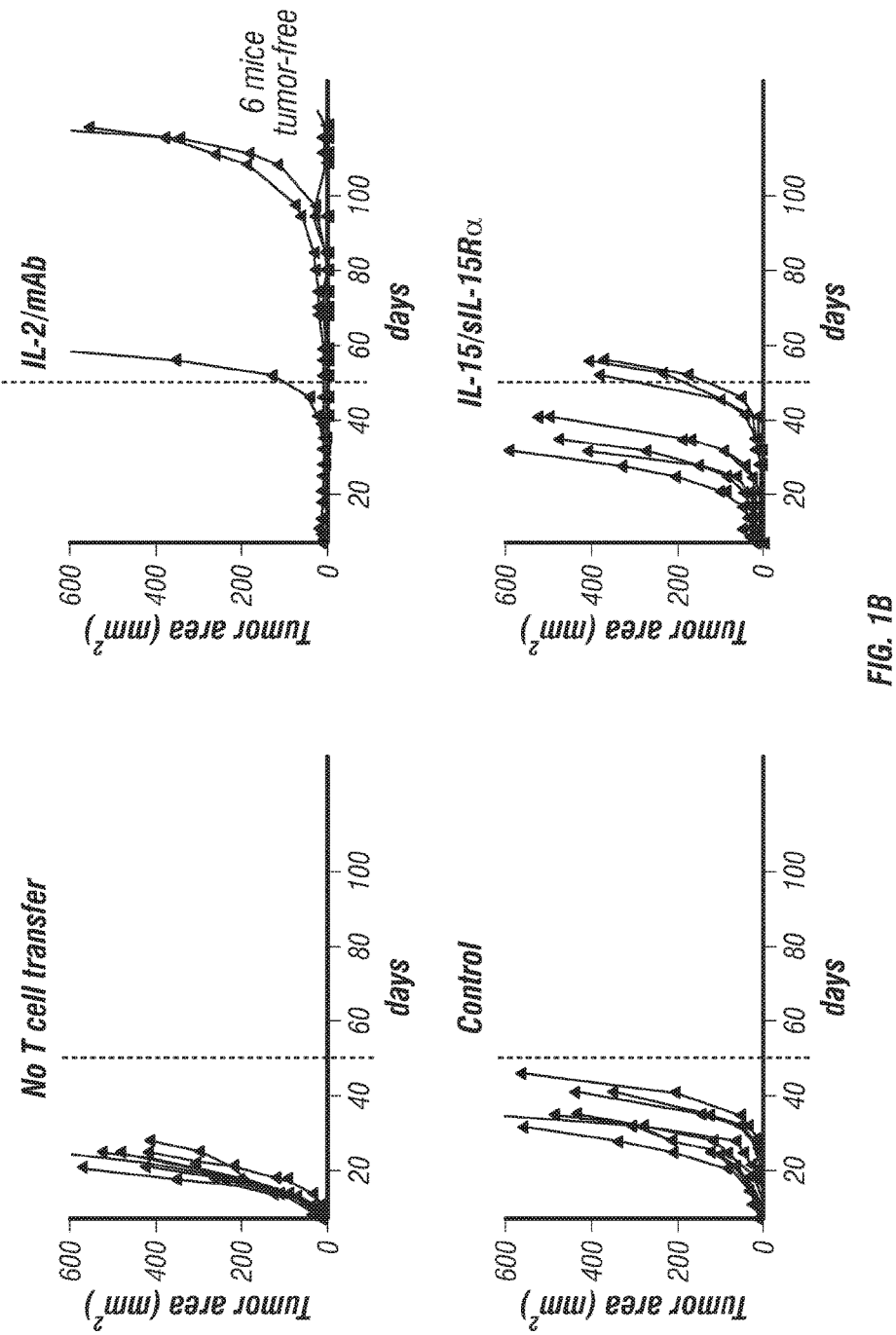

In some aspects, methods detailed herein concern adoptively transferring lymphocytes that have been modified to express elevated levels of cytokine receptor genes or cytokine receptor subunit genes. For example, tumor-reactive T cells can be modified to express IL-2Rα. Upon adoptive transfer, these cells will have enhanced ability to respond to the exogenous ligand. Thus, in this example, tumor-reactive T cells will have enhance ability to respond to exogenously administered IL-2 or a similar IL-2-based reagent. Cells responding to cytokine have significant advantage for growing and mediating effector functions such as killing tumor cells. Thus, this approach may allow clinicians to administer adoptive cellular therapy without having to precondition patients with chemotherapy or radiation to deplete host lymphocytes which normally compete for cytokine. Moreover, the instant methods provide the ability to genetically modify lymphocytes in vivo and provide them cytokine receptor genes or cytokine receptor subunit genes. For example, a subject may be injected with a retroviral vector containing IL-2Ra and a CD19-reactive CAR. Cells modified with such a vector would be very responsive to IL-2-based therapy, and therefore, this method would provide an effective means for expanding such cells. Methods, such those described above, have application for cancer therapy as well as for the treatment of other disease. For example, T regulatory cells might be genetically modified with IL-2Ra, and exhibit improved responsiveness to IL-2 therapy, and thus, this approach could have application for the treatment of autoimmune disease.

As noted above, in some specific examples, methods of the embodiments can be used to produce cells having enhanced responsiveness to IL-2. Administration of IL-2 is a critical component of many T cell-based strategies for cancer therapy. However, IL-2 has a short half-life and dose limiting toxicity. Furthermore, as IL-2 selectively expands T regulatory cells, it has been proposed that IL-15-based therapies may more effectively support adoptively transferred effector T cells. The findings here show that genetically transferring cytokine receptor genes, such as IL-2Rα, into lymphocytes or other cells dramatically enhances sensitivity to cytokine therapy. This approach is easily adopted for other cytokines or injectable protein therapeutics dependent on receptor expression. For example, the technique could be used to genetically transfer IL-15Rα to modulate lymphocyte responsiveness to IL-15. It is also possible to create chimeric or novel receptors combing different ligand binding and cell signaling properties. It is also possible to genetically add receptors in vivo through novel gene transfer techniques. Alternatively, in some instances, receptor genes may be introduced in a transient method (such as RNA electroporation), so that the impact is not long lasting.

In some embodiments, the treatment entails genetically modifying lymphocytes with other proteins that enhance cytokine receptor gene expression. This could include the transfer of transcription factors that lead to up-regulation of cytokine receptors or enhance the cellular machinery necessary for cytokine responsiveness.

In another embodiment, receptor expression is modulated in other ways than outlined above. For example, modulation of the levels of IL-2Rβ and IL-2Rγ, either individually, together, or with or without modulation of IL-2Rα, may be done. As part of this, modulation may be done by increasing the expression of these receptors or by inhibiting the expression of the endogenous receptor(s). For example, genetic modification of IL-2Rα and Il-2Rβ may be necessary for optimal responsiveness to IL-2.

As an additional aspect of the embodiments, mutant or altered versions of IL-2 may be used. For example, a mutant recombinant IL-2 molecule may be used to enhance binding to IL-2Rα. In some cases a mutant IL-2 may also have altered affinity for IL-2Rα dependent on pH (and thus, may undergo differential intracellular trafficking). The treatment may use an IL-2 molecule fused to another protein such as IgG. These altered IL-2 molecules may provide for improved IL-2 responsiveness and act in an additive or synergistic manner to the genetic modification of T cells as proposed above.

In another embodiment, altered receptor molecules are designed. For example, a version of IL-2Rα with improved sensitivity to IL-2 may be more effective upon genetic modification of lymphocytes.

In another embodiment, genetic constructs including long terminal repeats (LTR) linking T-cell receptor (TCR) or chimeric antigen receptor (CAR) genes to cytokine receptor subunits are created. For example, TCRα or TCRβ is linked to IL-2Ra, where the TCR genes are reactive against a melanoma tumor antigen. The genetic construct used could be a retroviral vector, lentiviral vector, or any other means of genetically modifying T cells using DNA or RNA. In addition to these genetic elements, other genes may be linked to this construct such as a selectable marker (CD34 or GFP) or a suicide gene to allow killing of the adoptively transferred cell population.

In some embodiments, this approach is used to modify other cells, such as specific lympohcyte subsets (such as T regulatory cells, Tc1 cells, or Th17 cells), or completely different classes of lympohcytes such as natural killer cells.

As detailed above, in some embodiments a method of treating a patient is provided. For example, in the case of a patient with metastatic melanoma, who seeks treatment with adoptive cellular therapy, tumor infiltrating lympohcytes (TIL) can be isolated from this patient and expanded to later numbers for adoptive transfer. During this process, the TIL can be genetically modified with a retroviral vector encoding an IL-2R gene. While normally, such a patient might be given lymphodepleting non-myeloablative chemotherapy with cyclophosphamide and fludarabine, with IL-2Rα-modified TIL, this patient may not require such chemotherapy to enhance TIL efficacy or may require a lower dose of chemotherapy. In this situation, the patient may be given low dose IL-2 therapy. Alternatively, the patient could be given another IL-2-based molecule such as an IL-2 fusion protein.

In a further example, a patient with B cell-derived malignancy, who seeks treatment with adoptive cellular therapy, can have peripheral blood genetically modified with a CAR vector also containing an IL-2Rα gene. In some cases, there may also be a suicide gene in this vector. The patient can be treated with the CAR-IL-2Rα-modified T cells and low dose IL-2. In this case, the patient may not require chemotherapy to suppress the host immune cells.

In another example, a patient with metastatic melanoma who seeks treatment with adoptive cellular therapy, can have tumor infiltrating lympohcytes (TIL) isolated and expanded to sufficient numbers for adoptive transfer. During this process, the TIL can be genetically modified with a retroviral vector encoding IL-12 receptor (IL-12Rβ1 and/or IL-12Rβ2). In this situation, very low doses of IL-12 may augment ability of TIL to mediate anti-tumor efficacy. In this case, IL-12 can be given at lower doses and may not be toxic to the patient. This example could be applied to any cytokine, ligand, or protein therapy where efficacy is impacted by dose limiting toxicity.

In still another example, a patient may require a bone marrow transplant. In this case, the bone marrow cells may be genetically modified with a vector encoding IL-2Rα, GM-CSF receptor (GM-CSF receptor α and βc), or G-CSF receptor (GCSF-receptor). In this case, the patient may be given GM-CSF or G-CSF ligand, to induce improved reconstitution of the bone marrow graft or IL-2 to selectively reconstitute T cells within the graft. This technology could be used with any cytokine or ligand receptor system.

Still another example of method of treatment in accordance with the embodiments concerns a patient with metastatic melanoma who seeks treatment with adoptive cellular therapy. Tumor infiltrating lympohcytes (TIL) can be isolated from this patient and expanded to sufficient numbers for adoptive transfer. During this process, the TIL can be genetically modified with a retroviral vector encoding a mutated IL-2Rα gene. The mutation may eliminate potential ribosylation sites, and therefore make the IL-2Rα more responsive to IL-2 therapy. Alternatively, the IL-2Rα molecule may be mutated so that the intracellular signaling domain from another receptor subunit or costimulatory molecule is engineered into the intracellular portion of IL-2Rα. In this case, the IL-2Rα may improve T cell function in novel ways. For this patient, while normally, he or she may be given lymphodepleting non-myeloablative chemotherapy with cyclophosphamide and fludarabine, with IL-2Rα-modified TIL, this patient may not require such chemotherapy to enhance TIL efficacy. In this situation, the patient may be given low dose IL-2 therapy. Alternatively, the patient could be given another IL-2-based molecule such as an IL-2 fusion protein.

II. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Study Design. This was a preclinical study to assess the efficacy of cytokine therapy to augment anti-tumor T cell immune responses. The inventors found that IL-2-based therapies were more efficacious than IL-15-based therapies in the tumor model, and thereafter, focused on understanding the mechanism of this differential response. For in vivo experiments, the numbers of mice are outlined in the figure legends. For all experiments, the number of independent replicates is outlined in each figure legend. Randomization and blinding for tumor experiments was done as described in the tumor methods below. Additional study design details are also included in the statistical analysis section below.

Recombinant Proteins and Antibodies. Human (h) IL-15, hIL-2, and anti-hCD3 mAb (clone OKT3) were kindly provided by the NCI Biological Resources Branch Preclinical Repository. Mouse (m) IL-2, mIL-12, and mIL-15 were purchased from Shenandoah Biotechnology. Recombinant sIL-15Ra-Fc (551-MR-100) and anti-hIL-2 mAb (clone 5355) were purchased from R&D systems. Anti-hIL-2 mAb$_{CD25}$ (clone 5344.111) was obtained from BD Bioscience. Anti-mIL-2 mAb$_{CD122}$ (clone S4B6) and anti-IL-2Rα (clone PC61) were obtained from Bioxcell. Anti-mIL-2 mAb$_{CD25}$ (clone JES6-1A12), anti-mCD3 mAb (clone 145-2C11), and anti-mCD28 mAb (clone 37.51) were obtained from the UCSF monoclonal antibody core. Antibodies used for flow cytometric and confocal analysis are described below.

Mice and Tumor Cells. C57BL/6 (B6), B6.PL (Thy1.1), B6(CD45.1), pmel-1 TCR transgenic, and OT-I TCR transgenic mice were purchased from Jackson Laboratory. All animals were housed under specific pathogen-free conditions in accordance with institutional and federal guidelines. For tumor experiments, B16-F1 cells were obtained from ATCC.

T cell cultures. Mouse Tc1 and Tc0 cells were generated from pmel-1 and OT-I TCR transgenic mice as previously described (Rubinstein et al., 2012). Briefly, splenocytes were cultured for three days with relevant peptide (for pmel-1, hgp100$_{25-33}$ peptide (KVPRNQDWL) (SEQ ID NO: 1) and for OT-I, OVA$_{257-264}$ peptide (SIINFEKL) (SEQ ID NO: 2) and cultured with (Tc1) or without (Tc0) mIL-12 (10 ng/ml). Polyclonal mouse T cells were generated by culturing B6 splenocytes for three days with plate-bound anti-CD3 mAb (clone 145-2C11, 1 ug/ml) unless otherwise stated. Activated human T cells were generated by culturing de-identified human PBMCs (Research Blood Components) from healthy adult donors for two or three days with plate-bound anti-CD3 mAb (clone OKT3, 1 ug/ml).

Tumor and Persistence Studies in Mice. For tumor experiments, B6 mice were challenged subcutaneously with 2.5× 10$^5$ B16-F1 tumor cells. Prior to randomizing mice to treatment groups, some mice were excluded due to abnormal tumor growth. As indicated, mice were treated by adoptive transfer of activated T cells (Tc1 or Tc0) by intravenous tail vein injection. Cytokine complexes were administered by intraperitoneal injection on days 0, 2, 4, and 6 after adoptive transfer unless otherwise indicated. Cytokine complexes used include: hIL-15/sIL-15Rα, hIL-15 (0.5 ug)/sIL-15Ra-Fc (2.3 ug); hIL-2/mAb, hIL-2 (1.5 ug)/anti-IL-2 mAb (7.5 ug, clone 5355); hIL-2/mAb$_{CD25}$, hIL-2 (1.5 ug)/anti-IL-2 mAb (7.5 ug, clone 5344.111); mIL-2/mAb$_{CD122}$, mIL-2 (1.5 ug)/anti-IL-2 mAb (7.5 ug, clone S4B6); and mIL-2/mAb$_{CD25}$, mIL-2 (1.5 ug)/anti-IL-2 mAb (7.5 ug, clone JES6-1A12). Tumor growth was measured by caliper every 2-4 days by personnel blinded to the treatment regimen. Tumor surface area (mm$^2$) was calculated as length×width. Mice were sacrificed when tumors reached 400 mm$^2$. For persistence studies, mice received adoptive transfer of activated T cells (Tc1 or Tc0). Peripheral blood lymphocytes or indicated organs were stained for CD8 and either Thy1.1 or CD45.1 to identify donor T cells. In experiments with a mixed transfer, the inventors used effector T cells from wildtype (Thy1.1) and IL-2Rα$^{+/-}$ (Thy1.2) mice that were activated with plate-bound anti-CD3/anti-CD28 mAb, mixed, and transferred into B6(CD45.1) mice.

Where indicated, mice also received total body irradiation (600 rad) one day prior to adoptive T cell transfer. In all adoptive transfer experiments, donor and recipient mice were gender-matched and were 6-12 weeks of age. All animals were housed under specific pathogen-free conditions in accordance with institutional and federal guidelines.

Flow Cytometry. Flow cytometry analysis was performed as previously described (17). The antibodies used in this study include CD8 (53-6.7), CD25 (PC61), CD45.1 (A20), IFNγ (XMG1.2), STAT5 pY694 (47/Stat5(pY694)), Thy1.1 (A20), and TNFα (TN3-19.12). These were purchased from BD Bioscience, Biolegend (San Diego, Calif.), and eBioscience (San Diego, Calif.). For analysis of phosphorylation of STAT5, the inventors followed the manufacturer's protocol using Lyse/Fix and PermIII buffer (BD Bioscience). To examine cellular proliferation, cells were fixed and permeabilized according to the manufacturer's protocol for Cytofix/Cytoperm (BD Bioscience) and stained with anti-Ki67 mAb (SolA15, eBioscience). Alternatively, BrdU (10 μm) was added one hour prior to harvest, and cells were analyzed for BrdU incorporation as previously described (Rubinstein et al., 2008). For Foxp3 staining, the inventors followed the protocol outlined in the Foxp3 kit (eBioscience). Flow cytometry was performed on BD LSRII and BD FACSAccuri. Data were analyzed using FlowJo software (TreeStar). In all experiments, initial gating of live cells was performed using forward scatter and side scatter parameters, and cells were then gated on live lymphocytes. Isotype and fluorescence minus one (FMO) controls were performed as required. For experiments assessing IL-2, the inventors always included control conditions without IL-2 pulsing.

In Vitro Experiments. For functional assays, Tc1 or Tc0 cells were incubated with cytokines and assayed for pSTAT5, Ki67, BrdU, or propidium iodide exclusion. For pulse assays, cells were incubated with or without cytokine at 200 ng/ml at either 4° C. or 37° C. for 90 minutes unless otherwise indicated. Cells were then washed at least three times, replated without cytokine, and assayed for pSTAT5.

When added during the pulse step, anti-IL-2Rα mAb was added 15 minutes prior to cytokine addition. Acid wash was performed by washing cells twice for 2 minutes at 4° C. with an acid wash buffer consisting of complete media adjusted to pH3.5 or pH3.75 with 1N HCl. For analysis of recycling of IL-2 to the cell surface, acid washed cells were replated in media at 37° C. for the indicated amount of time with anti-IL-2 mAb conjugated to Alexa647. To assess IFNγ and TNFα production, the inventors added hgp100$_{25-33}$ (1 ug/ml) or PMA (50 ng/mL) and ionomycin (1 μM) to splenocytes for 6 hours in the presence of brefeldin A (GolgiStop, BD Bioscience).

Confocal Microscopy. Tc1 cells were incubated with hIL-2 (200 ng/ml), mIL-2 (200 ng/ml), or no cytokine, for 1 hour at either 4° C. or 37° C. unless otherwise stated. Cells were washed, fixed, and permeabilized using the Cytofix/Cytoperm protocol. To determine the subcellular localization of internalized IL-2 by confocal microscopy, cells were stained with anti-hIL-2 mAb and either anti-IL-2Rα pAb (R&D systems), anti-Rab5 mAb (C8B1, Cell Signaling), anti-LAMP1 mAb (1D4B, company), or anti-EEA1 mAb (C45B10, Cell Signaling). To detect anti-IL-2Rα, the inventors used an anti-goat IgG conjugated to Alexa488 (R&D systems). To detect EEA-1 and Rab5, the inventors used an anti-rabbit IgG conjugated to Alexa488 (F(ab')2 fragment, Cell Signaling). After washing, cells were transferred to SuperFrost microscope slides via cytospin. Immunofluorescence staining was visualized with a confocal microscope (Olympus Fluoview FV10i laser scanning confocal microscope system, Olympus) using a 60× water immersion objective (1.2 NA). Image analysis was performed using the FV10-ASW 1.7 software. In all images, IL-2 staining is presented as a red pseudocolor. In all experiments, cells pulsed without IL-2 were used as the primary control.

Statistical Analyses. Before analysis, graphical displays were made of all data vs. conditions to identify the need for transformations to adhere to model assumptions. For experiments comparing outcomes at a fixed point in time, log transforms were taken and comparisons of means performed using two-sample t-tests or linear regression (depending on the number of conditions). Where appropriate, t-tests assumed unequal variance across conditions. Comparisons of conditions where mice were followed over time were made at individual timepoints based on random effects linear regression models (with random effects to account for correlation of data from the same mouse over repeated measures) with the outcome (e.g. % T-cells) log-transformed. Graphical displays were used to assess appropriateness of transformation. Residual plots were inspected to assess assumptions of linear regression models. Time to sacrifice was compared across groups using log-rank tests. Time to sacrifice was compared across groups using log-rank tests. Percent colocalization was compared with log (percent) as the outcome (due to skewness) and main effects of LAMP-1 (vs. EEA-1) and rater. The LAMP-1 effect was evaluated based on the Wald test of the regression coefficient. Model results were exponentiated to provide point estimates for LAMP-1 and EEA-1 colocalization. In the interest of addressing the hypotheses and not over-testing, the inventors did not perform hypothesis tests for every possible comparison in each figure. Where comparisons were insignificant (p>0.05) it is stated in the text; where tests were significant, it is stated and/or indicated with asterisks in figures. P-values are reported to two significant digits, except when the p-value is less than 0.001; for p-values smaller than 0.001, it is reported as 'p<0.001'. P-values are not corrected for multiple comparisons. For all analyses, statistical significance was based on a two-sided α level of 0.05. Statistical analyses were performed using Stata/IC (version 12.1) and R statistical software.

Example 2

Results

Figure 5A:
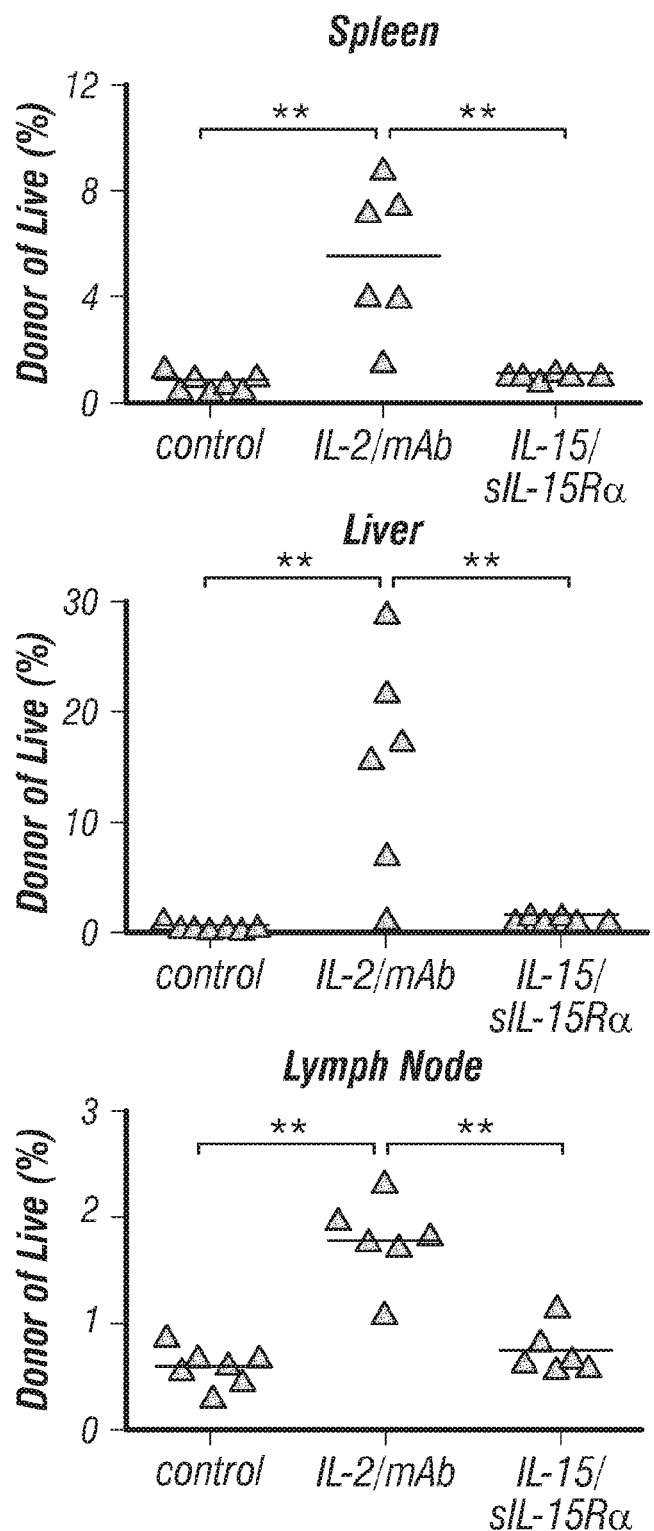
FIGS. 5a-5b—IL-2/mAb complexes selectively enhance the persistence of donor T cells. B6 mice (n=6-7/group) were injected intravenously with $8\times10^6$ Tc1 pmel-1 $CD8_+$ T cells. On days 0, 2, 4, 6, as indicated, mice received (i.p.) either hIL-2/mAb (clone 5355) or hIL-15/sIL-15Rα complexes. (a) The frequency of donor $CD8_+$ T cells in the spleens, lymph nodes and liver were determined on day 8. Each triangle represents one mouse and the bar indicates the mean. The symbol (**) indicates a significant difference (p<0.001) between indicated conditions. (b) Splenocytes from mice treated as in 'A' were stimulated with or without hgp100$_{25-33}$ peptide for 5 hours. The frequency of donor T cells positive for both IFNγ and TNFα was determined by flow cytometry. Results are representative of 2 independent experiments.
Figure 5B:
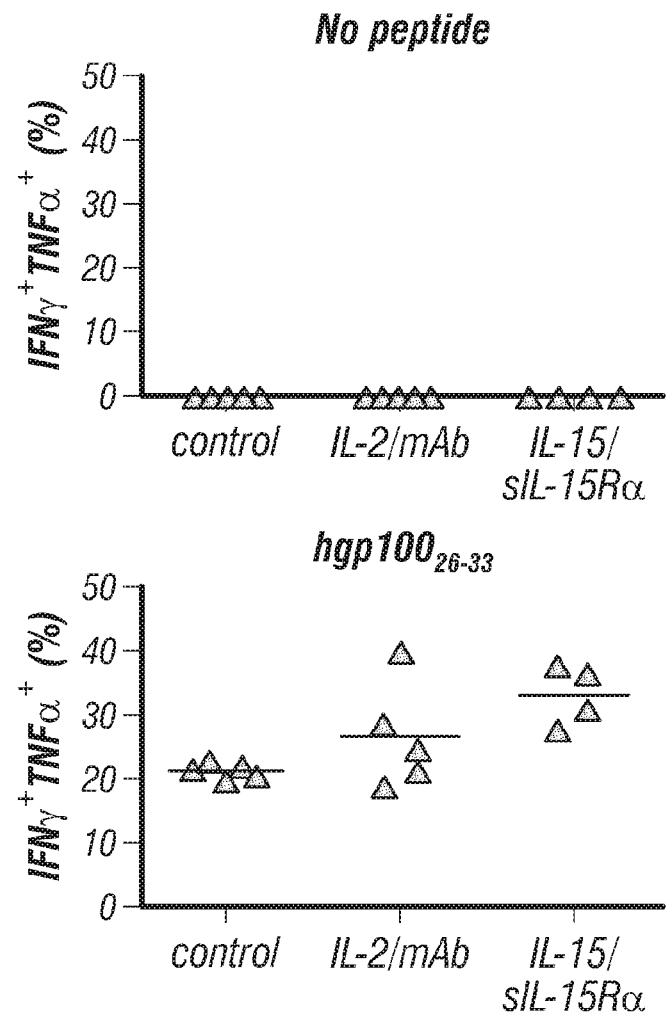
Figure 6:
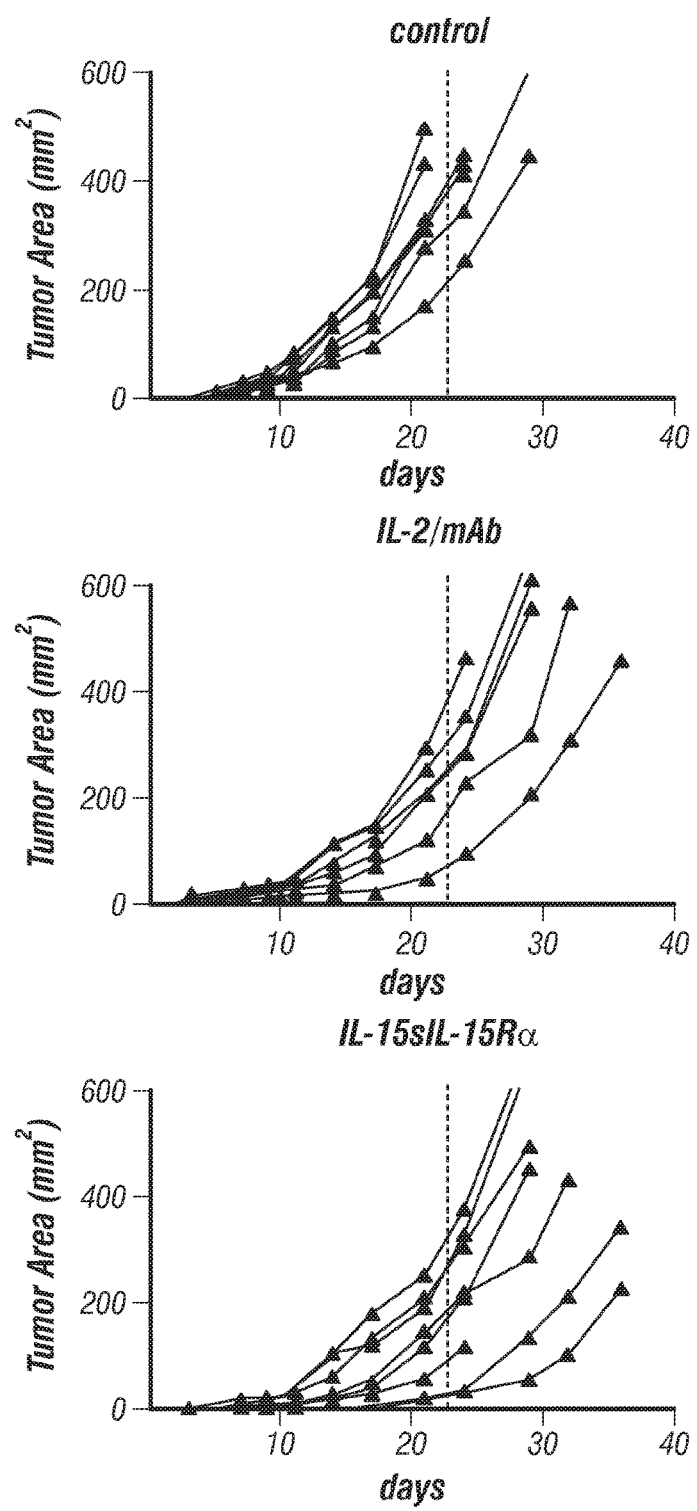
FIG. 6—In the absence of donor T cells, hIL-2/mAb and IL-15/sIL-15Rα complexes mediate comparable anti-tumor immunity. B6 mice (n=8/group) were injected with B16 tumor cells. The next day, mice were given i.p. injections as indicated of either hIL-2/mAb (clone 5355) or hIL-15/sIL-15Rα complexes for 7 days. (For hIL-2/mAb we used 1 μg of cytokine and 5 μg of antibody, and for hIL-15/sIL-15Rα we used 0.5 μg of cytokine and 2.3 μg of soluble receptor per injection.) Tumors were measured in a blinded fashion twice a week. Each line is representative of one mouse. IL-2/mAb and IL-15/sIL-15Rα complexes significantly increased the time to sacrifice versus the control condition (log-rank test, <0.05). Results are representative of 2 independent experiments.

IL-2—but not IL-15—Therapy Mediates Anti-Tumor Immunity after Adoptive Transfer of Activated CD8$^+$ T Cells. To assess the impact of cytokine therapy on adoptively transferred effector CD8$^+$ T cells, the inventors used IL-2/anti-IL-2 mAb (IL-2/mAb) and IL-15/sIL-15Rα-Fc (IL-15/sIL-15Rα) complexes, in which the antibody or receptor acts as a carrier molecule to improve the half-life and biological activity of free cytokine in vivo (Rubinstein et al., 2006; Stoklasek et al., 2006; Boyman et al., 2006). To test effector T cell responsiveness to cytokines in a clinically relevant model, B6 mice were injected (s.c.) with B16 melanoma tumor cells (FIG. 1A). After the establishment of palpable tumors, unirradiated mice received activated IL-12-conditioned T cells (Tc1) from pmel-1 TCR transgenic mice, from which CD8$^+$ T cells recognize an endogenous B16 tumor antigen (H-2D$^b$-restricted gp100$_{25-33}$ peptide). The inventors have shown these Tc1 effector cells are highly efficacious against tumor in lymphodepleted mice (Rubinstein et al., 2012). For the first week after adoptive transfer, IL-15/sIL-15Rα or IL-2/mAb (clone 5355) complexes were administered every 48 hours. While 6 of 9 mice that received IL-2/mAb complexes were cured of established tumor, mice that received either IL-15/sIL-15Rα complexes or no cytokine therapy showed no tumor regression (FIG. 1b). To better understand this differential response, the inventors assessed the persistence of donor Tc1 cells in recipients that received treatment with IL-2/mAb complexes or IL-15/sIL-15Rα complexes. Independent of the presence of tumor, only IL-2/mAb complexes enhanced the persistence of effector CD8$^+$ T cells in a systemic fashion across multiple organs (FIGS. 1c and 5a). Notably, without lymphodepletion or vaccination, the inventors routinely achieved sustained donor T cell frequencies of 20% or higher in the peripheral blood. Furthermore, donor Tc1 cells were equally functional across treatment groups as indicated by the ability to produce IFNγ and TNFα (FIG. 5b). Finally, as a control, the inventors found that the transfer of tumor-reactive effector CD8$^+$ T cells was necessary for curative therapy. Thus, tumor-bearing mice treated with only IL-2/mAb or IL-15/sIL-15Rα complexes exhibited minimally delayed tumor growth, albeit comparable between cytokine conditions (FIG. 6).

Figure 7:
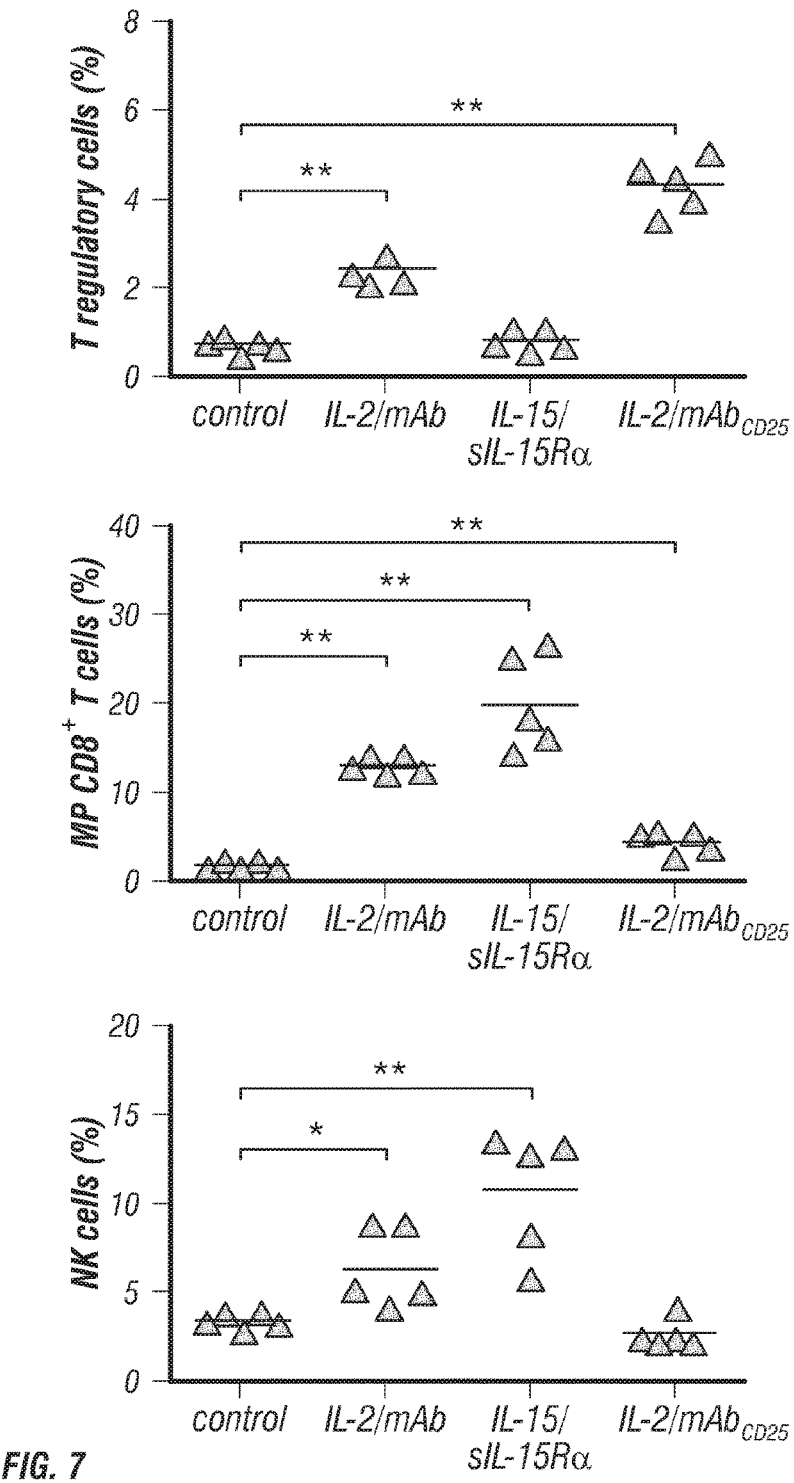
FIG. 7—Treatment with IL-2/mAb, IL-2/mAb$_{CD25}$, and IL-15/sIL-15Rα complexes induces differential expansion of $CD8_+$ memory-phenotype T cells, NK cells, and T regulatory cells. B6 mice (n=5/group) were injected with hIL-2/mAb (clone 5355), hIL-2/mAb$_{CD25}$ (clone 5344.111), or hIL-15/IL15Rα complexes on days 0, 2, 4, and 6. Spleens were harvested on day 8 and stained for T regulatory cells ($CD4_+CD25_+FOXP3_+$), memory-phenotype (MP) CD8 T cells ($CD8_+CD44^{hi}$), and NK cells (NK1.1$_+$TCRβ-B220$_-$). Mice also received adoptive transfer of Tc1 cells (data not shown). (**, p<0.001 or *, p=0.008) indicates a significant difference between indicated conditions and control. Data is representative of two independent experiments.
Figure 8:
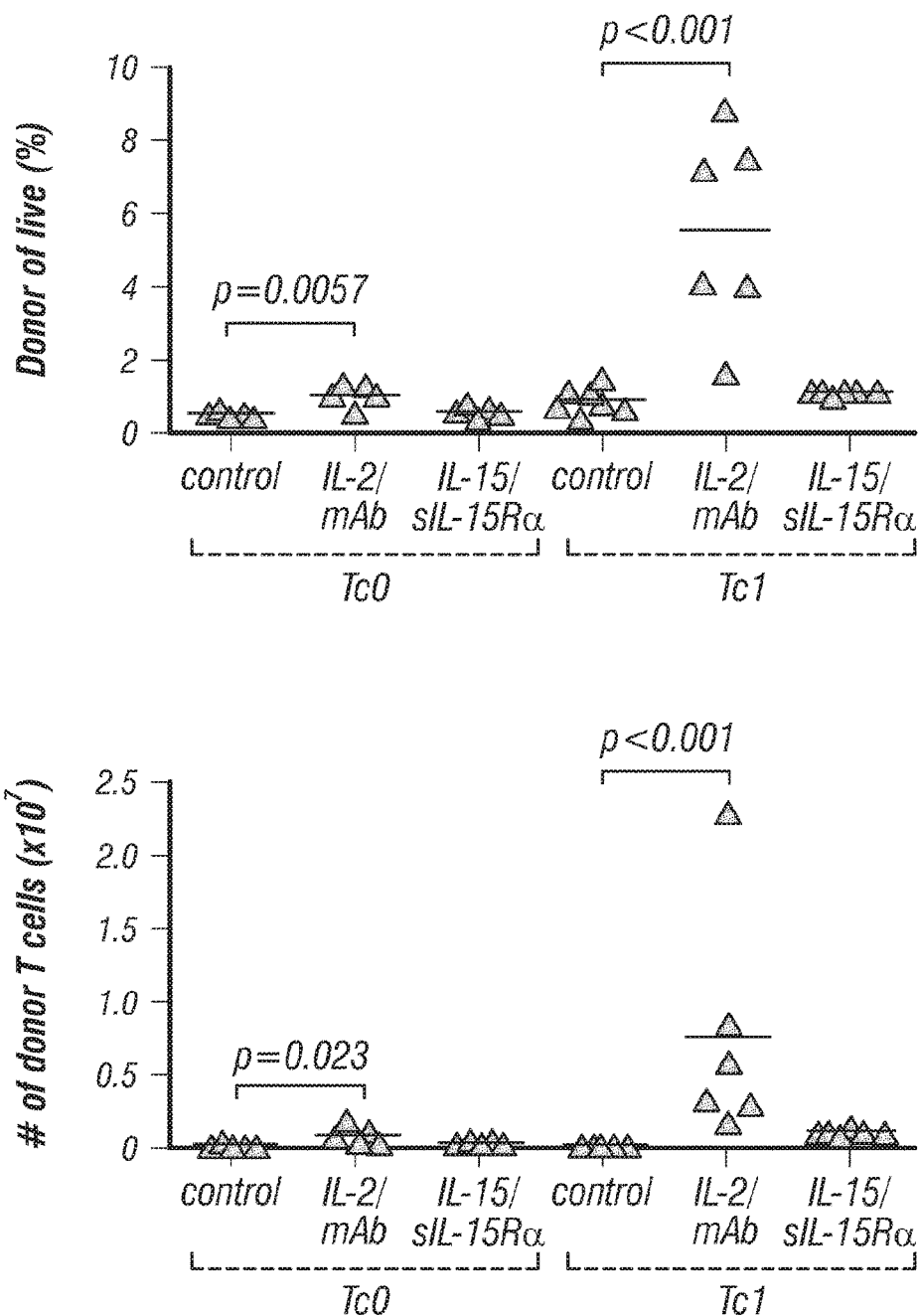
FIG. 8—Tc1 but not Tc0 effector $CD8_+$ T cells show preferential responsiveness to IL-2/mAb complexes. B6 mice (n=6-7/group) were injected intravenously with $8\times10_6$ Tc1 or Tc0 pmel-1 $CD8_+$ T cells. On days 0, 2, 4, 6, as indicated, mice received (i.p.) either hIL-2/mAb (clone 5355) or hIL-15/sIL-15Rα complexes. The top graph shows the frequency of donor $CD8_+$ T cells in the spleens on day 8. The bottom graph shows the absolute number of donor T cells on day 8. Each triangle represents one mouse and the bar indicates the mean. These data are from the same experiment shown in supplemental FIG. 1. Values were log-transformed prior to comparison of means by two-sample t-tests.

Donor T Cell Expression of IL-2Rα is Critical for Preferential IL-2-Mediated Responses. The preferential response of effector CD8$^+$ T cells to IL-2/mAb but not IL-15/sIL-15Rα complexes was contrary to the expectation. This response was not dose related as IL-2/mAb and IL-15/sIL-15Rα complexes expanded IL-2Rβγ$^{hi}$ cells such as memory-phenotype CD8$^+$ T cells and NK cells to a similar extent in vivo (FIG. 7) (Rubinstein et al., 2008). However, only IL-2/mAb complexes expanded T regulatory cells (FIG. 7), which are characterized by their expression of IL-2Rα. As IL-12-conditioned (Tc1) effector CD8$^+$ T cells express very high levels of IL-2Rα (Rubinstein et al., 2012), the results suggested an unappreciated role for cell surface IL-2Rα on effector T cells in dictating responsiveness to IL-2 therapy. To formally test this, the inventors made use of two anti-IL-2 mAbs with the ability to differentially redirect IL-2 based on lymphocyte cell surface IL-2Rα expression. IL-2/mAb$_{CD25}$ complexes (clone 1A12) preferentially expand IL-2Rα$^{hi}$ lymphocytes, while IL-2/mAb$_{CD122}$ complexes (clone S4B6) act in an IL-2Rα-independent manner (Boyman et al., 2006; Spangler et al., 2015). The inventors tested these two complexes in lymphoreplete mice injected with Tc1 cells. For only this experiment, the inventors generated Tc1 cells from another TCR transgenic mouse, OT-I, to confirm the results with a different TCR. While IL-2/mAb$_{CD122}$ complexes mediated a minimal increase in persistence, IL-2/mAb$_{CD25}$ complexes induced donor T cell levels of greater than 60% of total lymphocytes (FIG. 1d). To further confirm that this effect was dependent on IL-2Rα and not on IL-12 conditioning or selective TCR engagement, the inventors stimulated polyclonal T cells from wildtype mice with plate-bound anti-CD3 mAb, a method that generates IL-2Rα$^{hi}$ effector CD8$^+$ T cells. Upon adoptive transfer into lymphoreplete mice, IL-2/mAb complexes (clone 5355) greatly enhanced the persistence of polyclonal T cells (FIG. 1e). Finally, as an additional control, Tc0 cells, which have lower levels of surface IL-2Rα (Rubinstein et al., 2012), showed limited IL-2/mAb-driven persistence (FIG. 8).

Figure 2A:
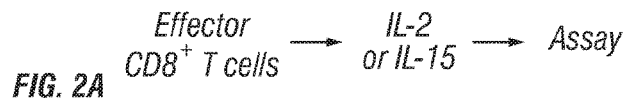
FIGS. 2a-2h—IL-2Rα mediates sustained signaling in effector CD8$^+$ T cells following withdrawal of IL-2. (a) Diagram of the standard cytokine assay in which effector cells are assayed after incubation with titrated cytokine. (b,c) Levels of pSTAT5 in Tc1 and Tc0 cells that were cultured with increasing amounts of mIL-2 or mIL-15 for 1 hour. (d) As in 'b', except Tc1 cells were incubated as indicated for up to 2 hours with 200 ng/ml of cytokine and assayed for pSTAT5. (e) Diagram of the cytokine pulse assay in which effector cells are incubated with saturating amounts of cytokine (200 ng/ml). Cells are then washed thoroughly, recultured at 37° C. without additional cytokine, and assayed for pSTAT5. (f) Levels of pSTAT5 in Tc1 cells that were pulsed with mIL-2 with or without anti-IL-2Rα mAb (PC61 clone) for 1 hour, washed, and recultured at 37° C. for the times indicated. (g,h) Levels of pSTAT5 in polyclonal effector T cells from wildtype (IL-2Rα$^{+/+}$) or IL-2Rα$^{+/-}$ mice that were pulsed for 1 hour with mIL-2 or mIL-15, and assayed as described in 'e'. Except for 'g' and 'h', all effector cells were generated from pmel-1 mice. All results are representative of at least 3 independent experiments.
Figure 2B:
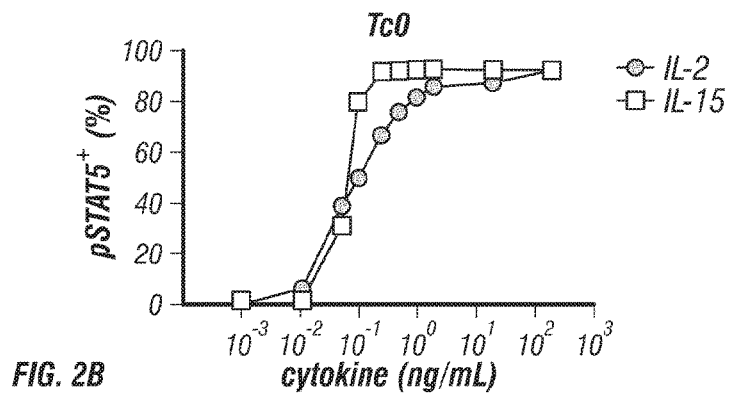
Figure 2C:
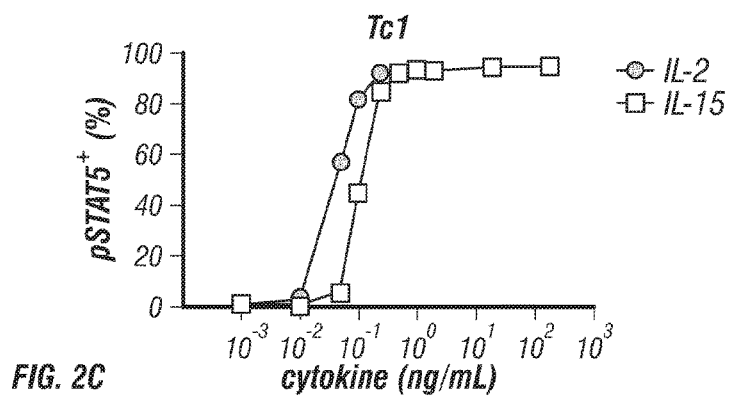
Figure 2D:
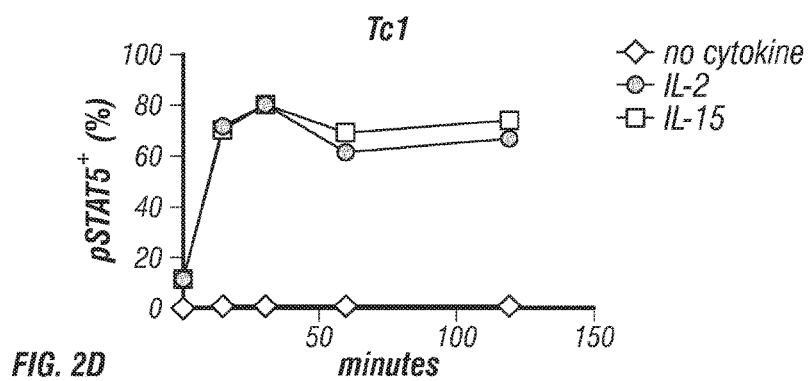
Figure 2E:
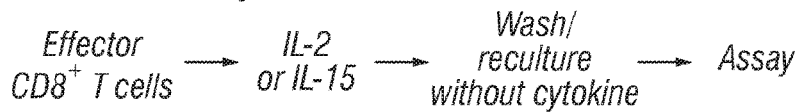
Figure 2F:
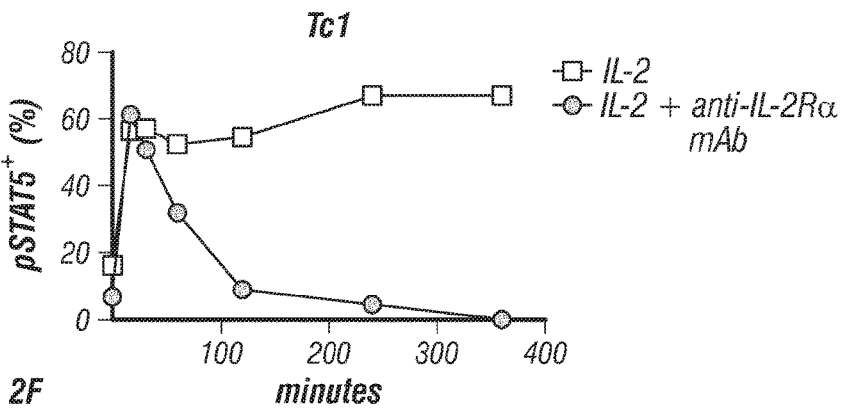
Figure 2G:
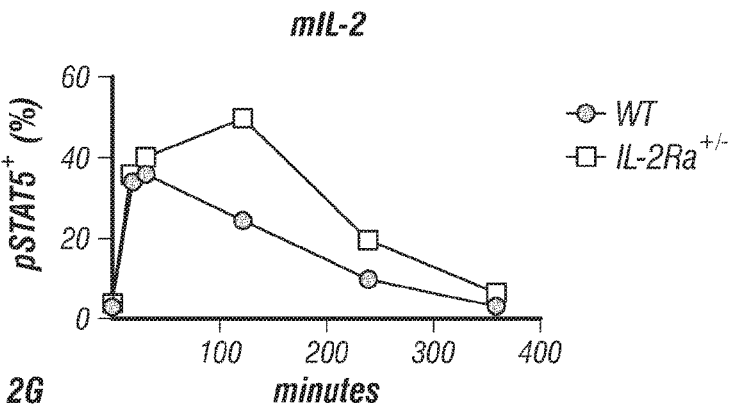
Figure 2H:
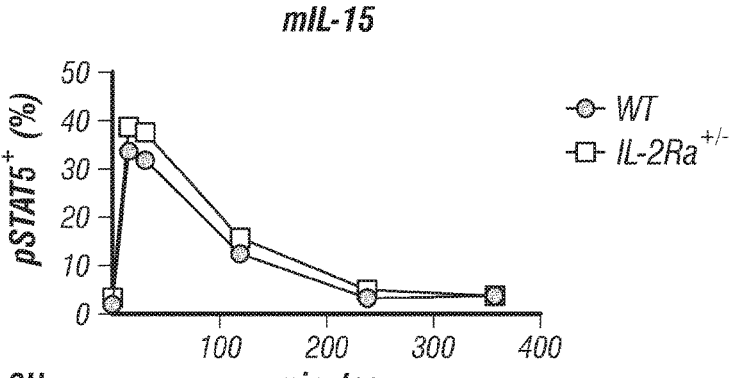
Figure 9A:
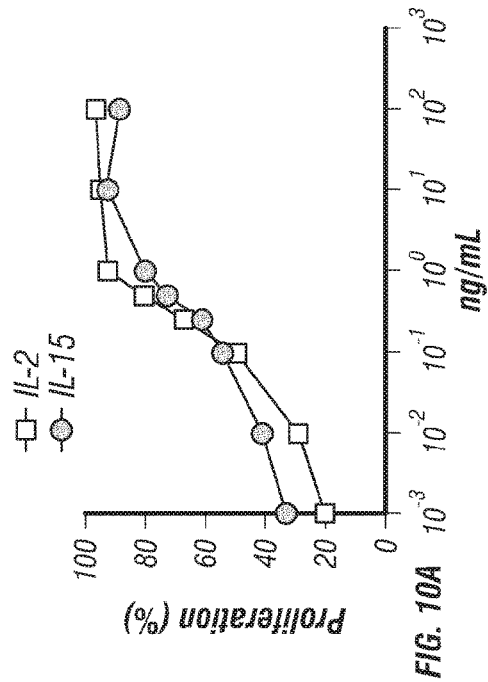
FIGS. 9a-9b—Blockade of IL-2Rα has minimal impact on Tc1 cells in response to titrated IL-2(a) or IL-15(b). Using a standard cytokine responsiveness assay, Tc1 cells from pmel-1 mice were incubated with titrated amounts of mIL-2 or mIL-15 for 30 minutes and assayed for pSTAT5. As indicated, anti-IL-2Rα mAb (PC61) was added at 5 μg/ml. Results are representative of 3 similar experiments.
Figure 10A:
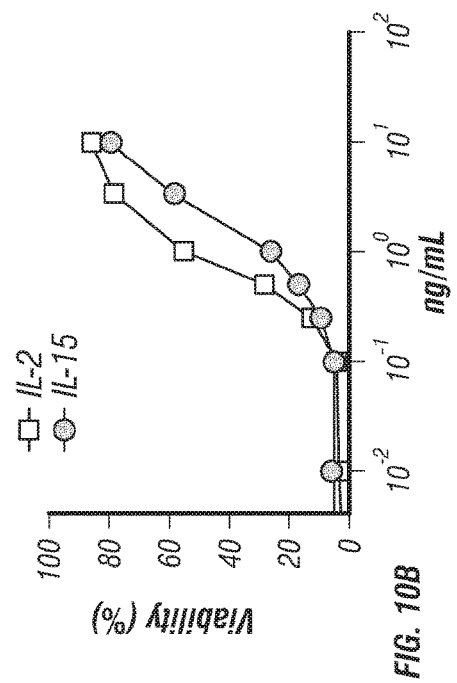
FIGS. 10a-10b—Tc1 effector $CD8_+$ T cells exhibit comparable functional sensitivity to IL-2 and IL-15 in vitro. Tc1 $CD8_+$ T cells generated from pmel-1 TCR transgenic mice were plated with either IL-2 or IL-15. After 48 hours, the frequency of proliferating (a) and viable (b) cells was assayed by Ki67 staining and propidium iodide (PI) exclusion, respectively. Cells were then analyzed by flow cytometry.
Figure 9B:
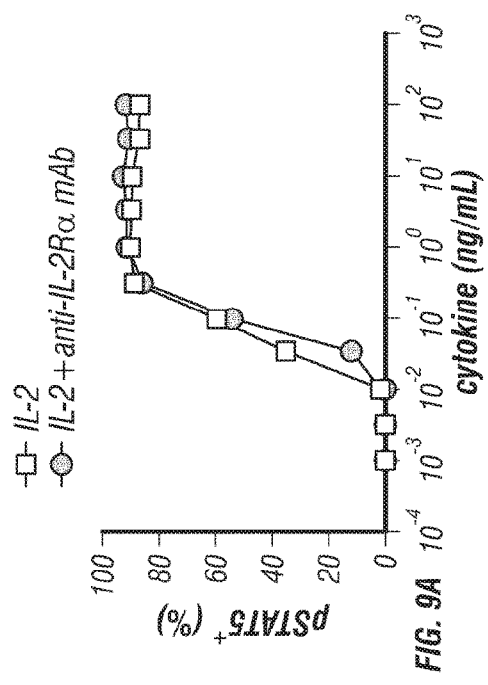
Figure 10B:
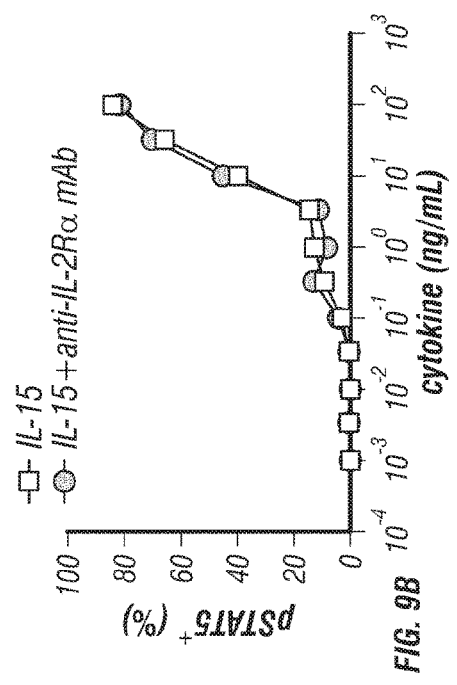
Figure 11A:
FIGS. 11a-11c—Tc1 effector $CD8_+$ T cells pulsed with IL-2 mediate sustained cytokine signaling. (a) In the cytokine pulse assay, Tc1 or Tc0 effector $CD8_+$ T cells were incubated overnight at 37° C. with mIL-2 (200 ng/ml), mIL-15 (200 ng/ml), or without cytokine. Cells were then washed thoroughly, recultured at 37° C. without additional cytokine, and assayed for phosphorylation of STAT5. The frequency of cells staining positive for pSTAT5 are shown for (b) Tc0 and (c) Tc1 cells. Results are representative of 3 independent experiments.
Figure 11B:
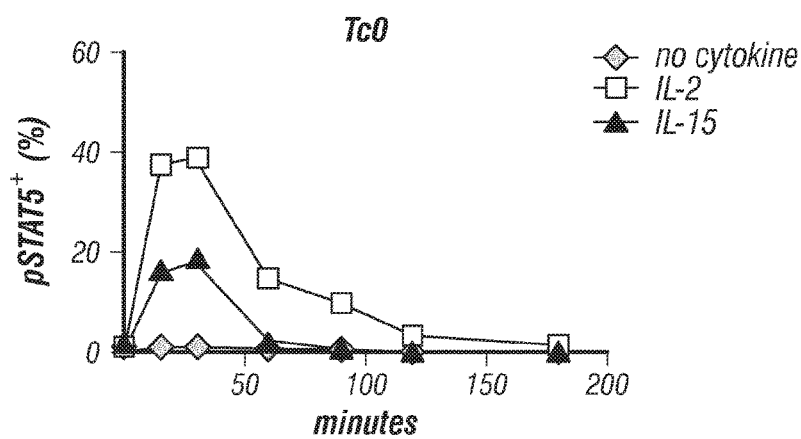
Figure 11C:
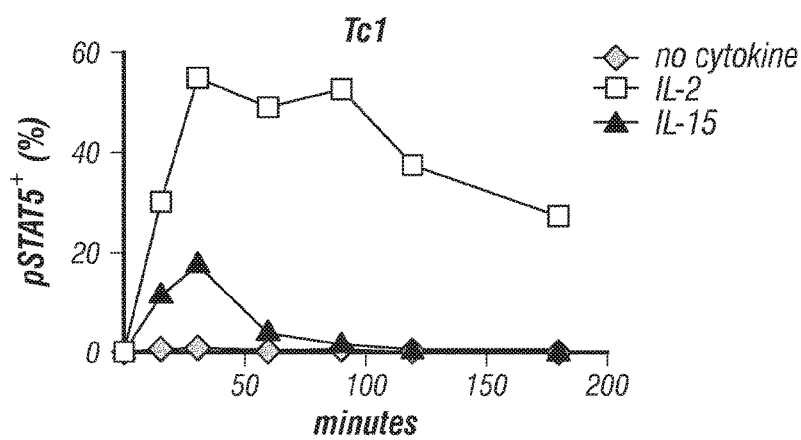
Figure 12:
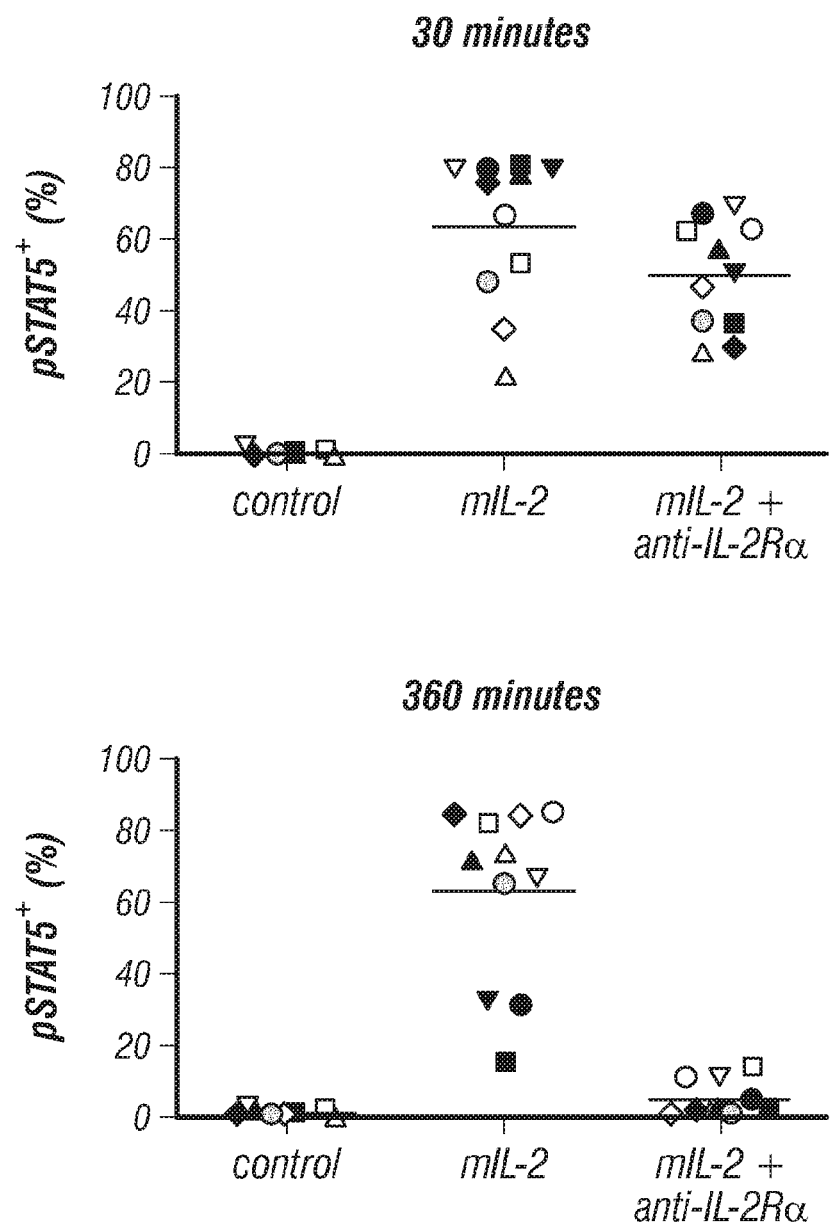
FIG. 12—IL-2 mediated sustained cytokine signaling is IL-2Rα-dependent in 11 independent experiments. Tc1 cells from pmel-1 mice were pulsed with mIL-2 with or without anti-IL-2Rα mAb (PC61 clone) for 90 minutes, then washed and recultured at 37° C. Cells were harvested at the times indicated and stained for pSTAT5. Each symbol represents one of 11 independent experiments.
Figure 13A:
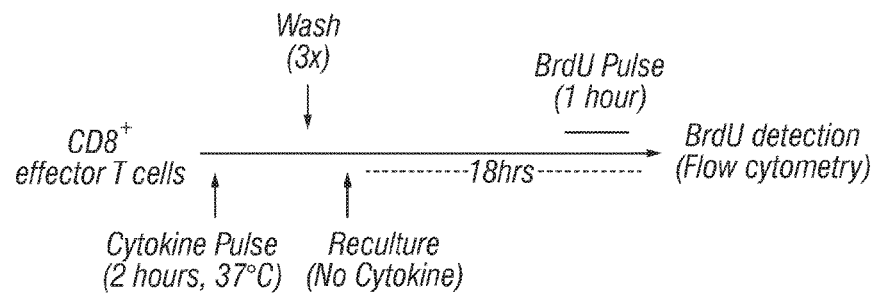
FIGS. 13a-13b-Tc1 effector $CD8_+$ T cells pulsed with IL-2 exhibit IL-2Rα-dependent proliferation after cytokine withdrawal. (a) Tc1 cells from pmel-1 TCR transgenic mice were pre-incubated as indicated with anti-IL-2Rα mAb (PC61) or isotype control antibody for 15 minutes. Then, mIL-2 or mIL-15 was added for 2 hours at 37° C. Cells were then washed three times and resuspended in culture media without cytokine for 18 hours. During the last hour of culture, BrdU was added. Cells were then stained for BrdU and CD8, and analyzed by flow cytometry. (b) The frequency of $CD8_+$ T cells positive for BrdU staining in cytokine-treated cultures is indicated by the black line and the number in the upper right quadrant. Control cultures without cytokine are indicated by the shaded histogram. Results are representative of 3 independent experiments.
Figure 13B:
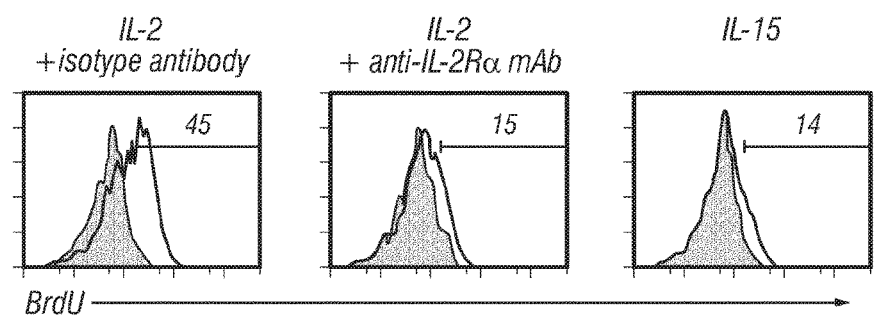
Figure 14:
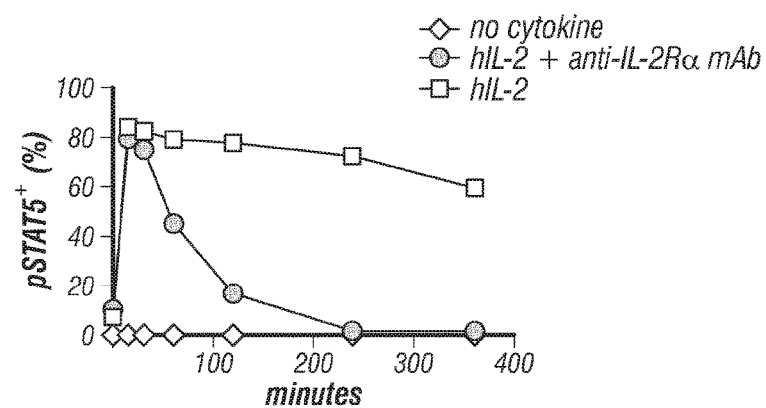
FIG. 14—Human IL-2 mediates sustained cytokine signaling on mouse Tc1 effector $CD8_+$ T cells. Tc1 cells from pmel-1 mice were pulsed with hIL-2 with or without anti-IL-2Rα mAb (PC61 clone) for 90 minutes, then washed and recultured at 37° C. Cells were harvested at the times indicated and stained for pSTAT5. Results are representative of 5 independent experiments.
Figure 16A:
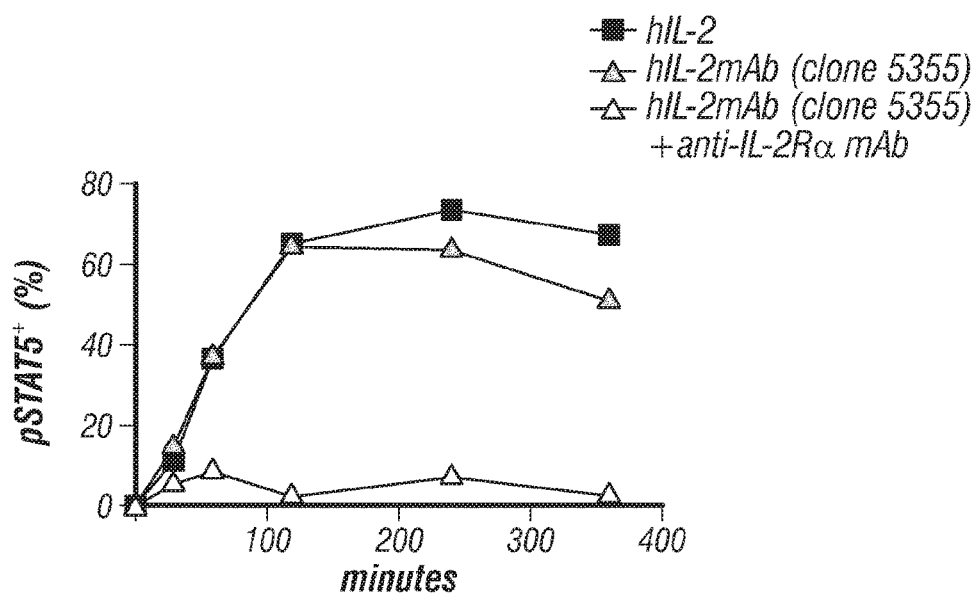
FIGS. 16a-16b—Human IL-2/mAb (clone 5355), but not mouse IL-2/mAb$_{CD122}$ (clone S4B6) complexes, are permissive to IL-2Rα-dependent sustained signaling in vitro. (a) Tc1 cells from pmel-1 TCR transgenic mice were incubated with hIL-2 with or without excess anti-hIL-2 mAb (clone 5355, 10 μg/ml) to generate hIL-2/mAb in vitro. In replicate wells, anti-IL-2Rα mAb (clone PC61) was added during the incubation step to block IL-2Rα-dependent signaling. Cells were then washed and recultured at 37° C. for the time indicated. Phosphorylation of STAT5 was assessed at the indicated time points by flow cytometry. (b) As in 'a', except mouse IL-2 and anti-mIL-2 mAb (clone S4B6, 10 μg/ml) were used to generate mL-2/mAb$_{CD122}$ in vitro. Results are representative of two independent experiments.
Figure 16B:
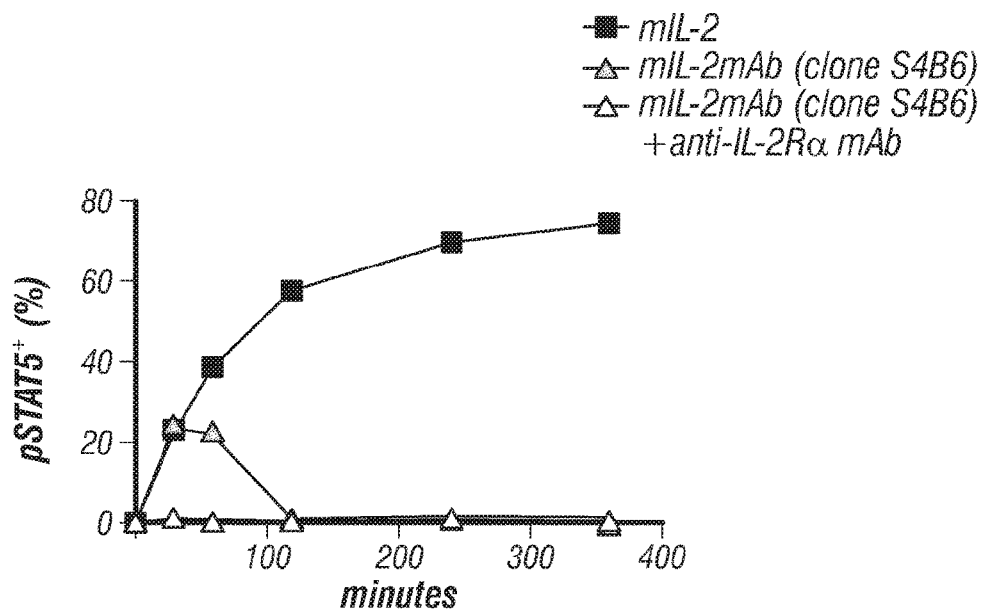

IL-2Rα Induces Sustained IL-2 Signaling in Effector CD8$^+$ T Cells after Cytokine Withdrawal. To uncover the mechanism behind the remarkable IL-2Rα-dependent responsiveness of effector Tc1 cells in vivo, the inventors assayed IL-2 and IL-15 activity downstream of IL-2Rβγ using standard in vitro assays quantifying phosphorylation of STAT5 (a proximal signaling event), viability, and proliferation (FIG. 2a). In the context of STAT5 phosphorylation in response to titrated cytokine, the inventors found that Tc1 (IL-2Rα$^{hi}$) cells exhibited marginally increased sensitivity to IL-2 versus IL-15 when compared to Tc0 effector cells (IL-2Rα$^{med}$) (FIGS. 2b-2c), which is consistent with previous findings (Lisiero et al., 2011). The addition of a blocking antibody (anti-IL-2Rα mAb, PC61 clone) also showed a minimal benefit of IL-2Rα engagement on Tc1 cells in comparison between titrated IL-2 and IL-15 (FIGS. 9a-9b). Notably, Tc1 cells responded comparably to IL-2 and IL-15 in standard assays of proliferation and viability (FIGS. 10a-10b). Importantly, there was no difference in the kinetics of STAT5 phosphorylation between cells cultured in IL-2 or IL-15 (FIG. 2d). The mildly enhanced sensitivity of Tc1 cells to IL-2 versus IL-15 seemed unlikely to account for the dramatic difference in activity observed in vivo. Therefore, the inventors hypothesized that IL-2Rα does not simply improve cellular affinity for IL-2, but allows for sustained IL-2 signaling after a T cell transitions from a cytokine-rich to a cytokine-free environment. To test this idea, the inventors used a cytokine pulse assay. Tc1 and Tc0 cells were cultured overnight with a saturating dose of IL-2 or IL-15, washed, and replated without cytokine as shown in FIG. 2e. Consistent with the hypothesis, only pre-culture of Tc1 cells with IL-2 led to sustained STAT5 phosphorylation in the absence of additional cytokine (FIGS. 11a-11e). To directly test the role of IL-2Rα in promoting sustained signaling on effector CD8$^+$ T cells, the inventors cultured Tc1 cells for 90 minutes with IL-2 in the absence or presence of blocking anti-IL-2Rα antibody (PC61 clone). This shorter pulse was equally sufficient for inducing sustained signaling as indicated by STAT5 phosphorylation (FIG. 2f). Importantly, blockade of IL-2Rα completely abolished the sustained IL-2 signaling as indicated by STAT5 phosphorylation and proliferation (FIGS. 2f, 12, and 13a-13b). Polyclonal effector CD8$^+$ T cells activated in the absence of IL-12 also showed sustained IL-2 signaling, and importantly, effector cells generated from IL-2Rα$^{+/-}$ mice showed roughly half the sustained IL-2 signaling (FIG. 2g). To ensure that these cells had similar IL-2Rβγ signaling potential, the inventors pulsed wildtype and IL-2Rα$^{+/-}$ effector CD8$^+$ T cells with IL-15 and found no differences in their response (FIG. 2h). Notably, the ability to induce sustained IL-2 signaling on mouse effector cells was observed with human and mouse IL-2 (FIG. 14). Furthermore, culture of human effector T cells with hIL-2 but not hIL-15 led IL-2Rα-dependent sustained STAT5 phosphorylation (FIGS. 15a-15b). Finally, to verify that IL-2/mAb complexes (clone 5355) used in the in vivo experiments were permissive to engagement of IL-2Rα, the inventors repeated the pulse assay with hIL-2 and excess anti-IL-2 mAb. In vitro generated IL-2/mAb complexes induced sustained IL-2 signaling that was dependent on IL-2Rα (FIG. 16a). In contrast, IL-2/mAb$_{CD122}$ complexes (clone S4B6), which do not engage IL-2Rα (Boyman et al., 2006; Spangler et al., 2015), failed to induce sustained signaling in vitro (FIG. 16b).

Figure 3A:
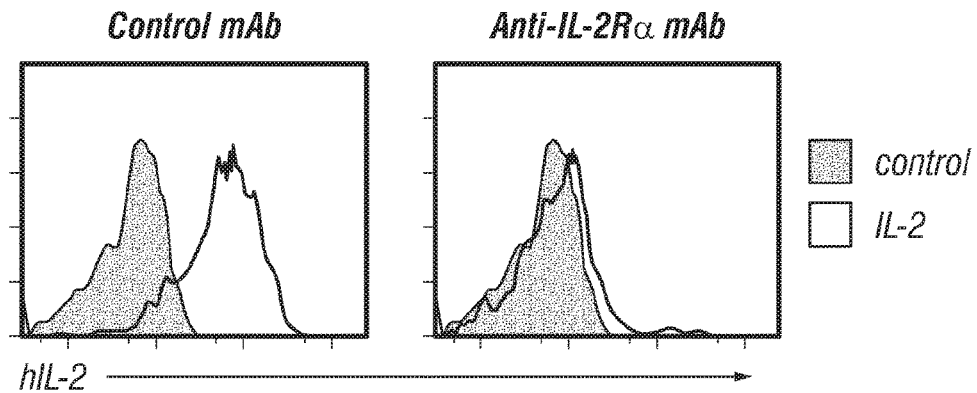
Figure 3B:
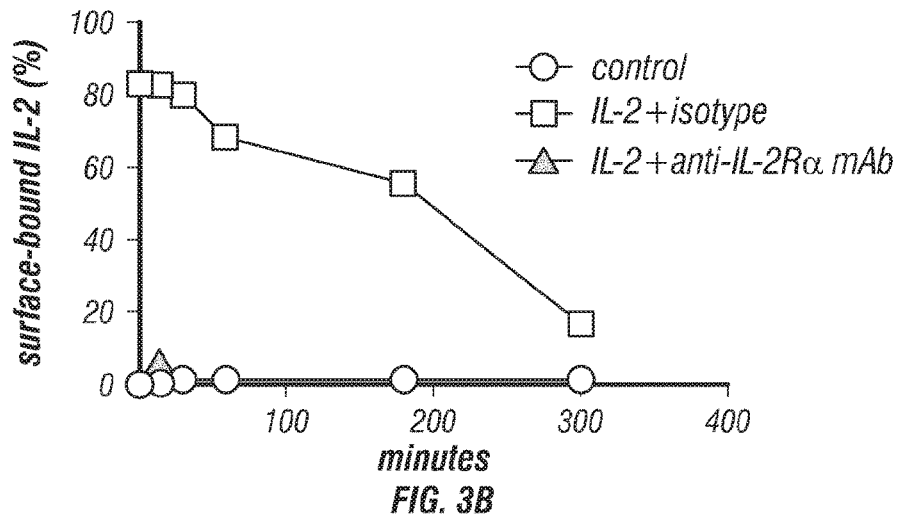
Figure 3C:
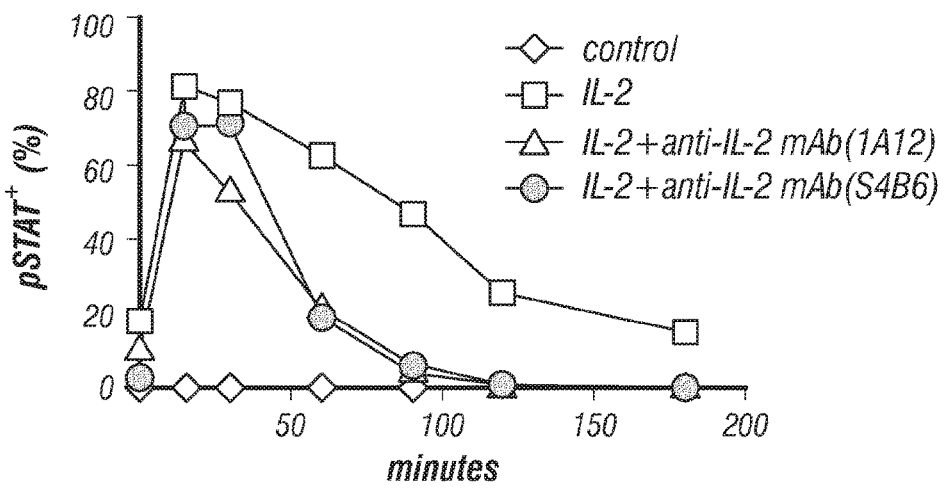
Figure 3D:
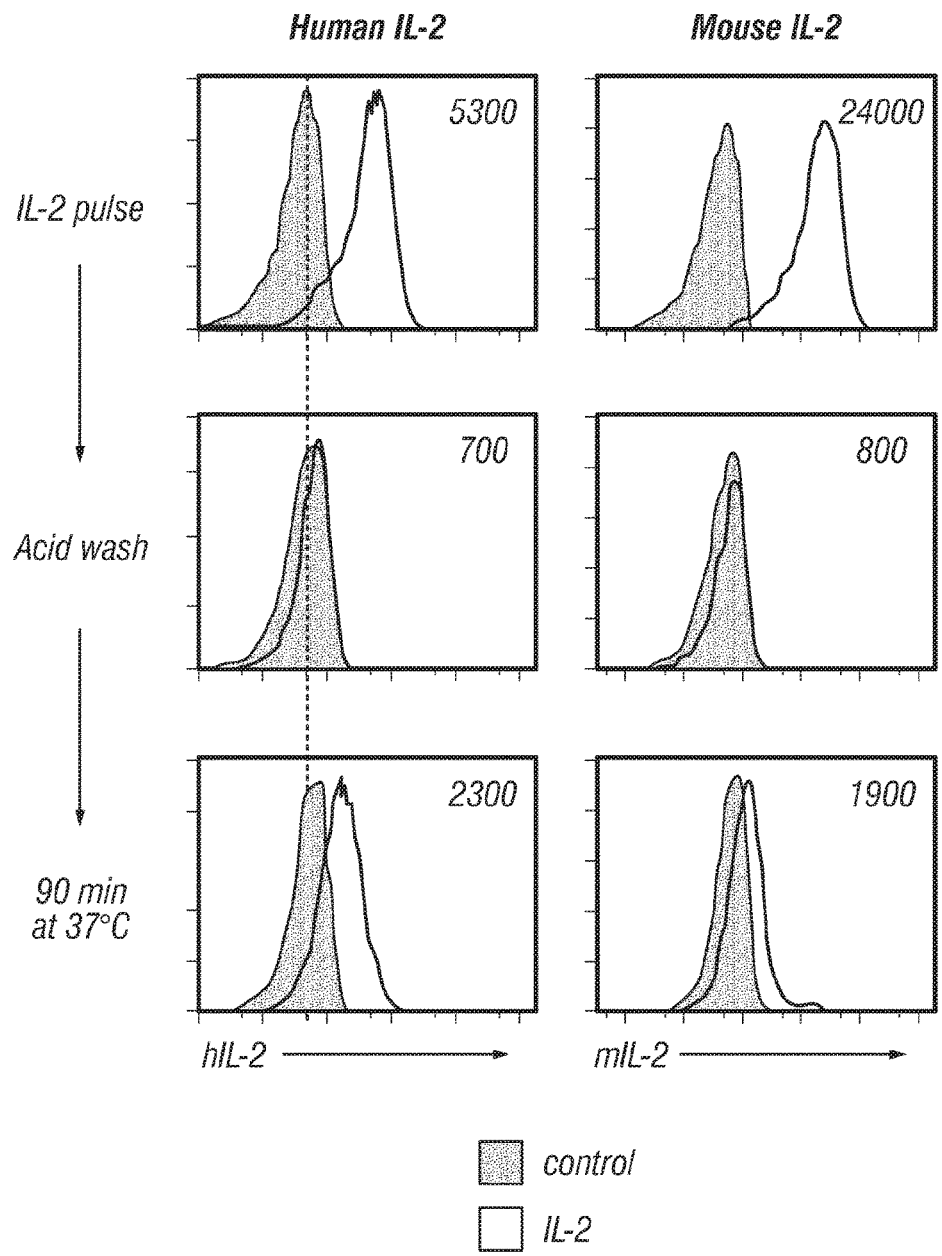
Figure 3G:
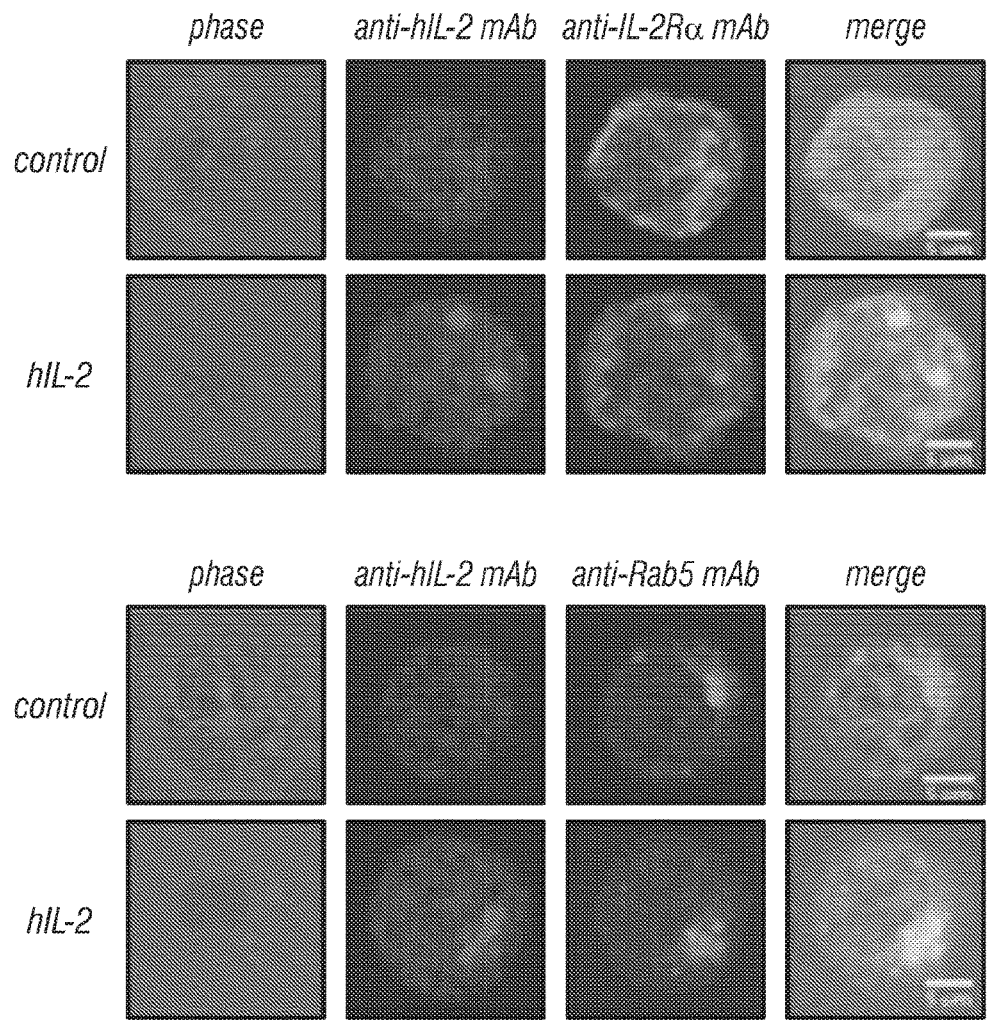
Figure 17:
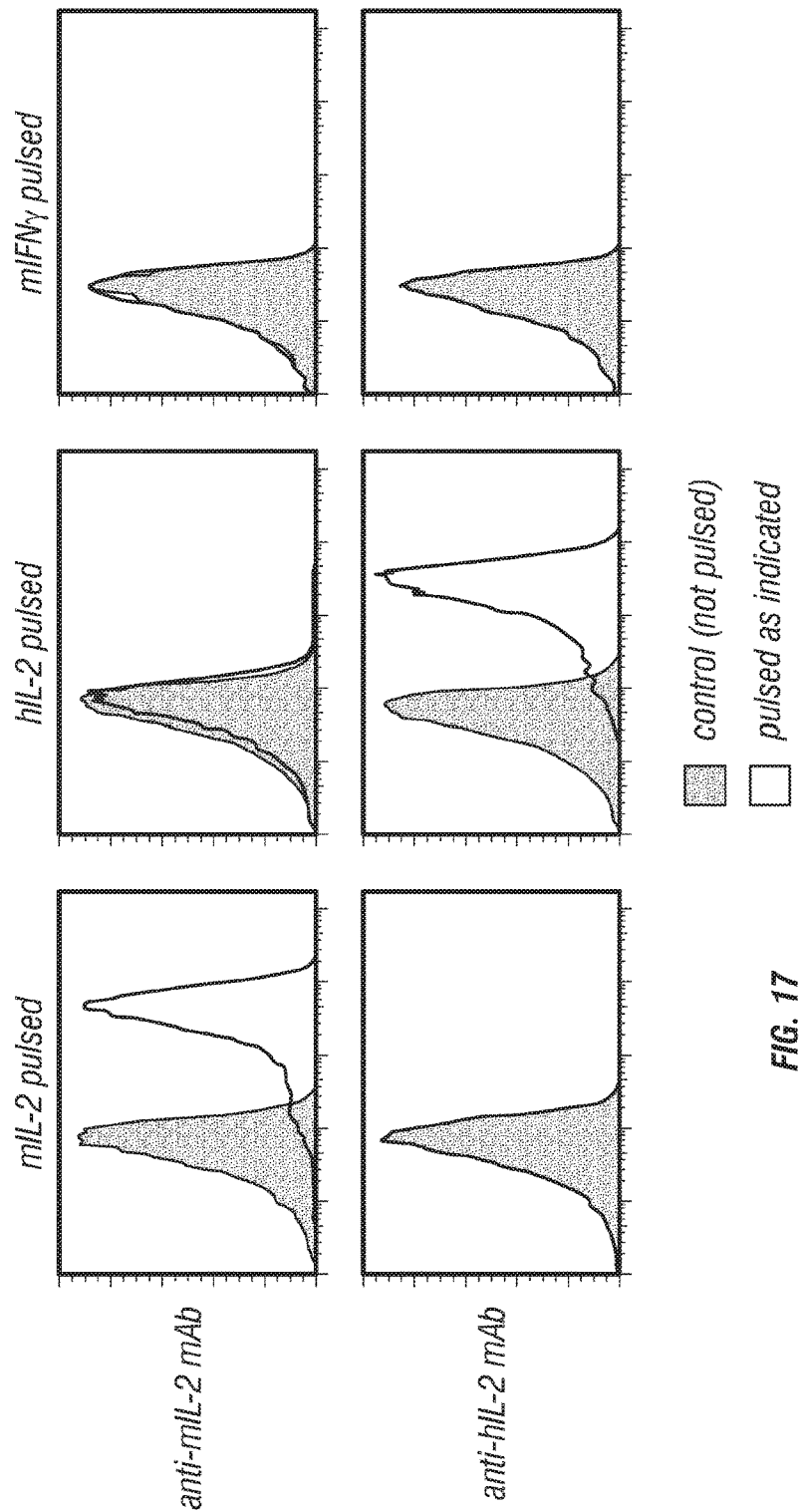
FIG. 17—Antibodies for mouse and human IL-2 are species-specific. Tc1 cells from pmel-1 TCR transgenic mice were pulsed with mIL-2 (200 ng/ml), hIL-2 (200 ng/ml), or mIFNγ (200 ng/ml) for 45 minutes. Cells were then stained with either anti-mIL-2 mAb or anti-hIL-2 mAb directly conjugated to Alexa647 and analyzed by flow cytometry. Data are representative of 3 independent experiments.
Figure 18A:
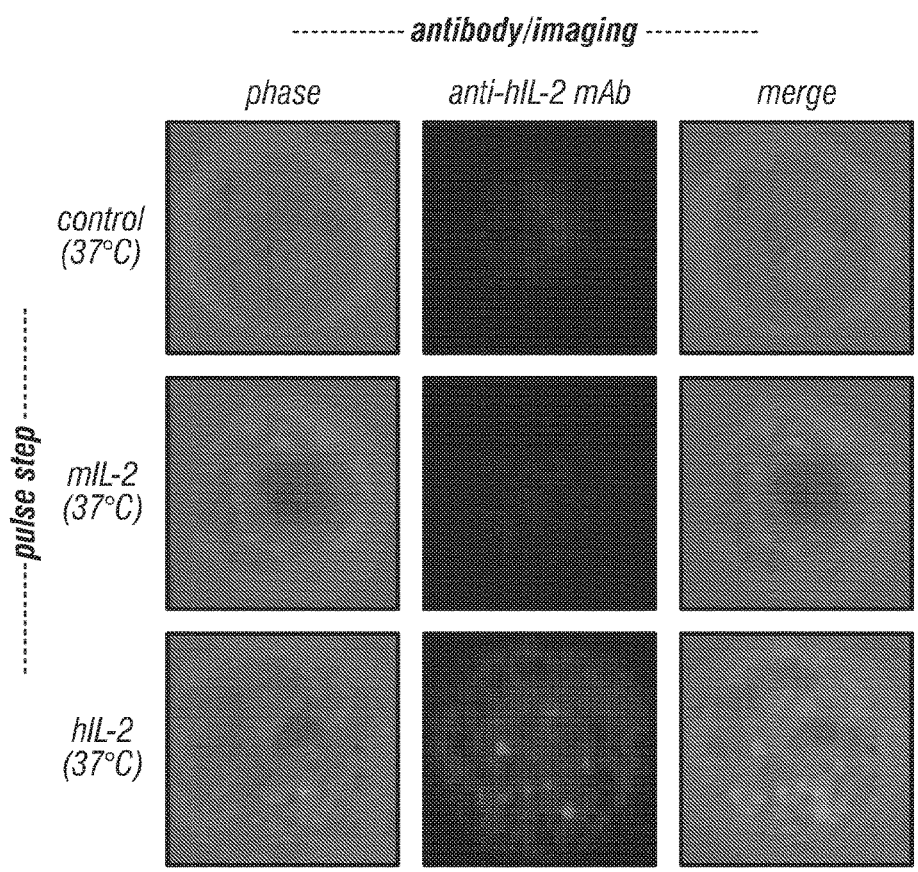
FIGS. 18a-18b—Detection of hIL-2 by confocal microscopy is species-specific and dependent on pulsing cells with cytokine at 37° C. (a) Tc1 cells generated from pmel-1 TCR transgenic mice were pulsed with hIL-2 (200 ng/ml), mIL-2 (200 ng/ml), or media alone (control) for 90 minutes at 37° C. Cells were then fixed, permeabilized, and stained with anti-hIL-2 mAb prior to being mounted onto slides. IL-2 staining in confocal images is represented as a red pseudocolor. (b) As in 'a', except cells were pulsed with hIL-2 at 4° C. or 37° C. All results are representative of at least two independent experiments.
Figure 18B:
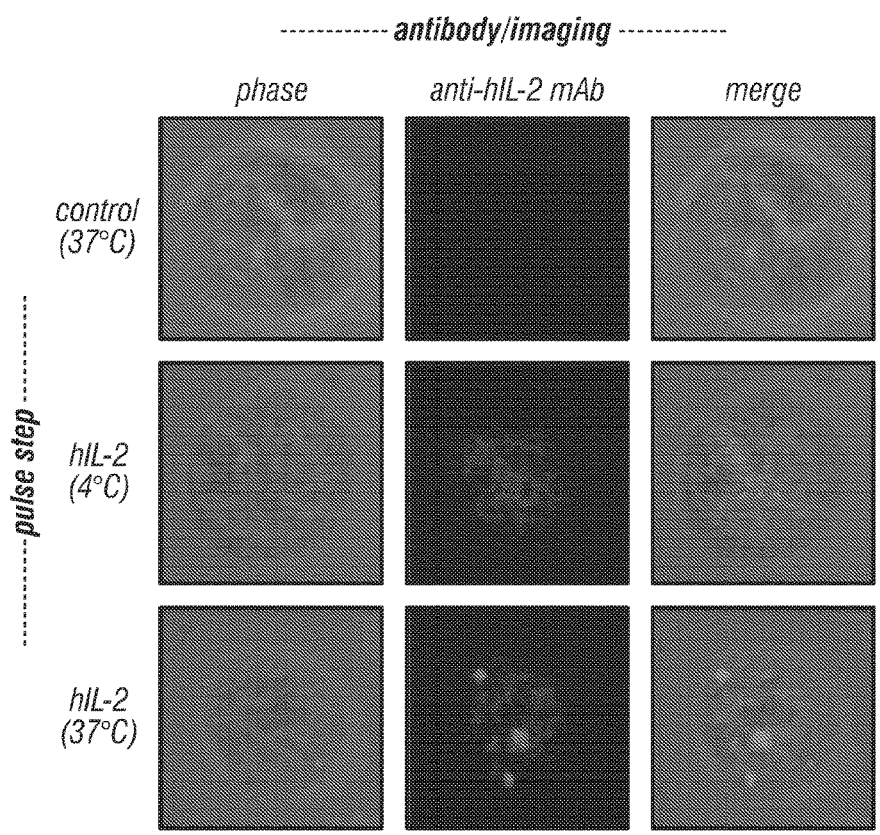
Figure 19:
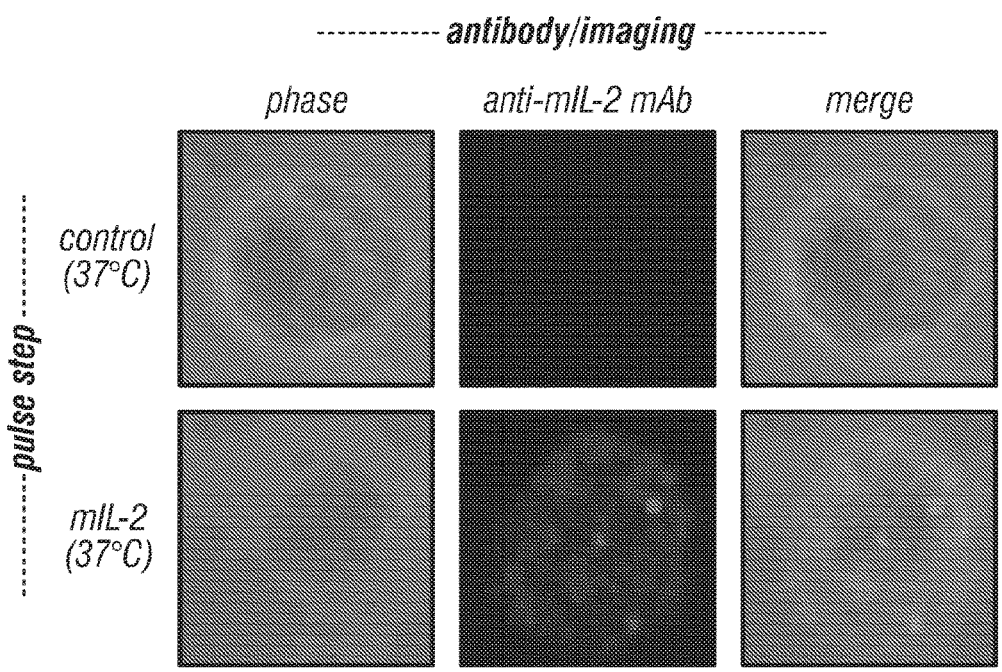
FIG. 19—Detection of mIL-2 by confocal microscopy. (a) Tc1 cells generated from pmel-1 TCR transgenic mice were pulsed with mIL-2 (200 ng/ml) or media alone (control) for 90 minutes at 37° C. Cells were then fixed, permeabilized, and stained with anti-mIL-2 mAb prior to being mounted onto slides. Results are representative of two independent experiments.
Figure 20A:
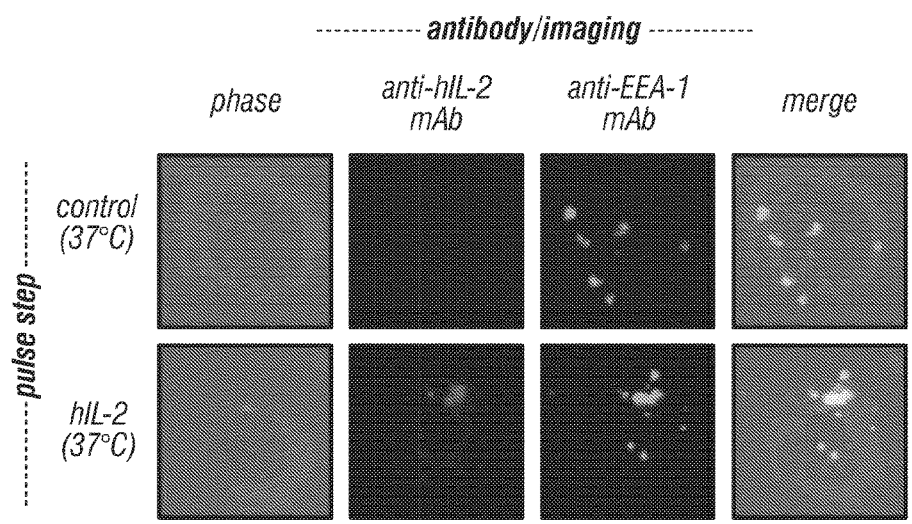
FIGS. 20a-20c—Colocalization of hIL-2 with EEA-1 and LAMP-1 by confocal microscopy. Tc1 cells from pmel-1 TCR transgenic mice were pulsed with hIL-2 for 90 minutes at 37° C., and stained for hIL-2, EEA1, or LAMP-1. Cells were then imaged by confocal microscopy to determine the subcellular localization of hIL-2 relative to EEA-1 and LAMP-1. Nine representative images for EEAVIL-2 and LAMP-1/IL-2 were taken, and scored blindly by three independent observers. The percent colocalization was determined by counting the sum of IL-2 directly colocalizing (yellow) versus IL-2 colocalizing (yellow) plus IL-2 alone (green). Each solid line below denotes readings by one rater of % colocalization of EEA-1 and LAMP-1. "X" values and dashed line indicate estimated colocalization from regression model, adjusting for rater variability. Mean difference in LAMP-1 and EEA-1 colocalization is statistically significant (p=0.010).
Figure 20B:
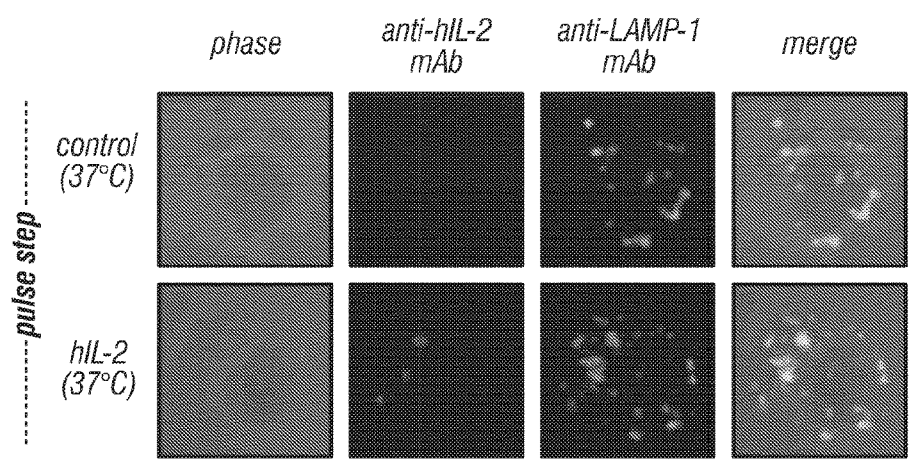
Figure 20C:
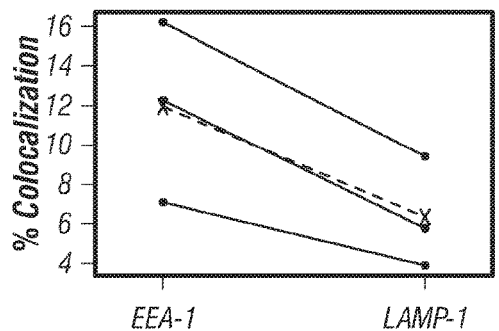

IL-2Rα Facilitates Sustained IL-2 Signaling Through Creation of an Extracellular Reservoir and Recycling. To understand how IL-2Rα promotes sustained IL-2 signaling, the inventors hypothesized two non-mutually exclusive possibilities. First, IL-2Rα may bind IL-2 and create a cell-surface cytokine reservoir due to the high ratio of surface IL-2Rα to IL-2Rβγ, as IL-2/IL-2Rα internalization can only occur in the presence of both IL-2Rβ and γ (Robb and Greene, 1987; Takeshita et al., 1992). Such a reservoir of IL-2 bound to IL-2Rα would mediate gradual signaling by continually feeding the rate-limiting, endocytosed IL-2Rβγ. In support of this possibility, the inventors detected high surface levels of IL-2 on effector CD8$^+$ T cells that gradually waned after extended culture, and this cell-surface IL-2 was dependent on available IL-2Rα (FIGS. 3a-3b). Furthermore, antibodies against IL-2 added after the removal of free cytokine from IL-2 pulsed cells were able to dampen sustained signaling (FIG. 3c). A second possible way in which IL-2Rα might sustain signaling is by promoting recycling of IL-2 from within the cell to the surface, thus allowing for repetitive signaling. To test this hypothesis, Tc1 cells were pulsed with IL-2 at 37° C. to allow for cytokine internalization. Cells were then stripped of surface IL-2 using an acid wash. Upon reculture at 37° C., the inventors were able to detect re-appearance of either mIL-2 or hIL-2 on the cell surface (FIG. 3d). Minimal surface IL-2 was observed when cells were pulsed at 4° C. or on the surface of mixed bystander Tc1 cells (FIG. 3e). Importantly, the species-specificity of the reagents precluded autocrine production as the source of cell surface IL-2 after acid wash (FIG. 17). In additional support of IL-2Rα-mediated recycling, the inventors observed sustained pSTAT5 signaling after acid washing of cells pulsed with hIL-2 at 37° C. but not 4° C. (FIG. 3f). Because internalization of IL-2Rαβγ does not occur at 4° C., these data provide further support that sustained signaling occurs in part through an IL-2Rα bound pool of internalized IL-2. It is notable that the inventors could not block sustained STAT5 signaling in cells pulsed with mIL-2 at 4° C. by acid washing, possibly reflecting a higher affinity of mIL-2 for mIL-2Rα compared with that of hIL-2 for mIL-2Rα (Spangler et al., 2015; Liu et al., 1996). Finally, confocal microscopy showed discrete punctate structures of either mIL-2 or hIL-2 when cells were incubated with cytokine at 37° C. but not 4° C. (FIGS. 18a, 18b, and 19). These punctate structures colocalized with IL-2Rα, Rab5, and EEA1, but less frequently with LAMP-1, consistent with intracellular IL-2 being accessible to the recycling pathway (FIGS. 3g, 3h and 20a-20c) (Grant and Donaldson, 2009; Mu et al., 1995). Taken together, these results suggest that IL-2Rα both promotes an extracellular reservoir for IL-2 and mediates recycling of IL-2.

Figure 4A:
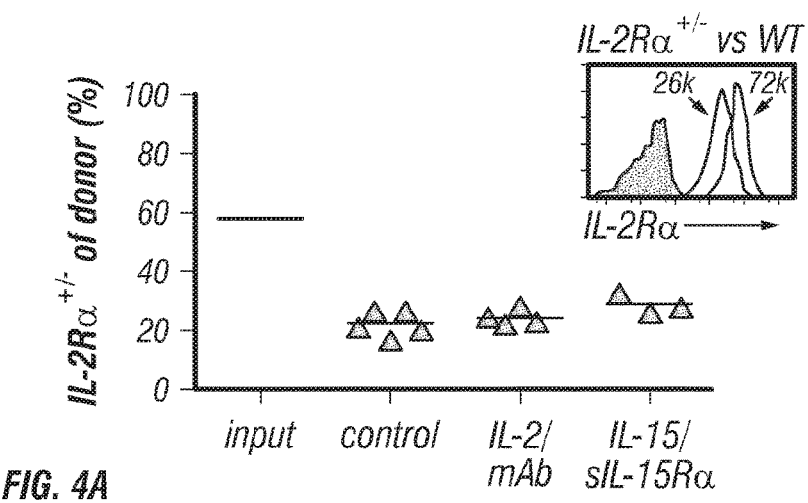
FIGS. 4a-4c—IL-2Rα on donor T cells is critical for persistence in lymphoreplete but not lymphodepleted hosts. (a) Wildtype and IL-2Rα$^{+/-}$ effector CD8$^+$ T cells show similar persistence with or without IL-2 therapy. Effector T cells from wildtype and IL-2Rα$^{+/-}$ mice were activated, mixed, and injected into recipient mice (n=3-5/group). Mice received injections of hIL-2/mAb (clone 5355) complexes, hIL-15/sIL-15Rα complexes, or vehicle alone. The proportion of IL-2Rα$^{+/-}$ T cells among all donor T cells in the spleen was determined pre- and post-transfer. Each triangle represents one mouse and the bars indicate the mean. (b) The total number of donor T cells per spleen for the experiment shown in 'a'. The bars indicate the mean. The symbol () indicates a significant difference (p<0.001) between indicated conditions. (c) The total number of donor T cells in the spleen for the experiment shown in 'a'. Mice (n=5/group) were given total body irradiation (TBI, 600 rad) one day prior to adoptive transfer of 10$^7$ Tc1 (pmel-1) cells, and then treated with hIL-2/mAb (clone 5355) or hIL-15/sIL-15Rα complexes. The frequency of donor T cells in the blood of mice was determined at the indicated time points. Each point represents the average and bars indicate standard error. The symbol () indicates a significant difference (p<0.001) between control and indicated conditions. All results are representative of 2 independent experiments.
Figure 4B:
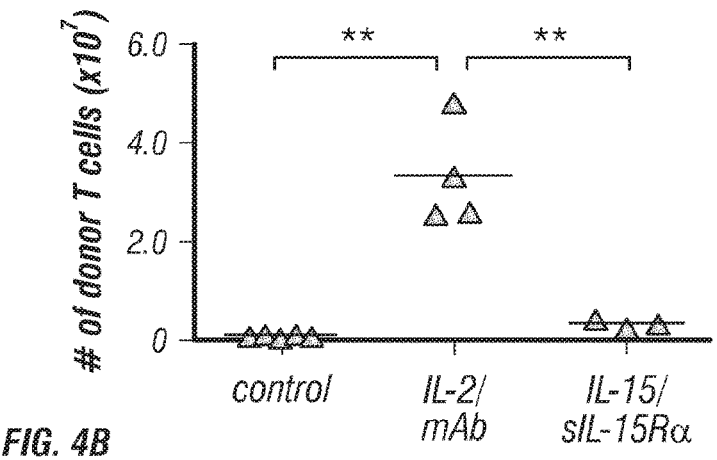

IL-2Rα Expression on Donor CD8+ T Cells Provides a Competitive Advantage to IL-2 Therapy in a Lymphoreplete but not Lymphopenic Host Environment. The results thus far suggest that the differential responsiveness of Tc1 cells to IL-2- and IL-15 therapy in vivo is a consequence of IL-2Rα on donor T cells providing a competitive advantage to accessing cytokine. To formally test this hypothesis, the inventors initially attempted to activate T cells from wild-type and IL-2Rα$^{-/-}$ mice. However, this proved technically not feasible for us as T cells isolated from IL-2Rα$^{-/-}$ mice were resistant to normal activation, likely due to the immune alterations in the absence of IL-2 responsiveness (Willerford et al., 1995). Therefore, the inventors used polyclonal IL-2Rα$^{+/-}$ T cells, as these cells activated comparably to wildtype T cells and had approximately half the expression of IL-2Rα (FIG. 4a). Using the Thy1.1 congenic marker to distinguish between genotypes, these two cell populations were mixed and adoptively transferred into non-irradiated B6(CD45.1) recipient mice. Mice were treated with IL-2/mAb or IL-15/sIL-15Rα for 1 week. The inventors hypothesized that IL-2Rα$^{+/-}$ donor CD8+ T cells would not persist as well as their wildtype counterparts due to loss of one allele. In contrast to the expectations, wildtype and IL-2Rα$^{+/-}$ donor T cells did not show differential responsiveness to treatment with IL-2/mAb or IL-15/sIL-15Rα complexes (FIG. 4a-4b). These results suggest a threshold of IL-2Rα in vivo, both in terms of level and durability of expression, that when reached is sufficient for providing donor cells a competitive advantage to IL-2 therapy in a lymphoreplete environment.

Figure 4C:
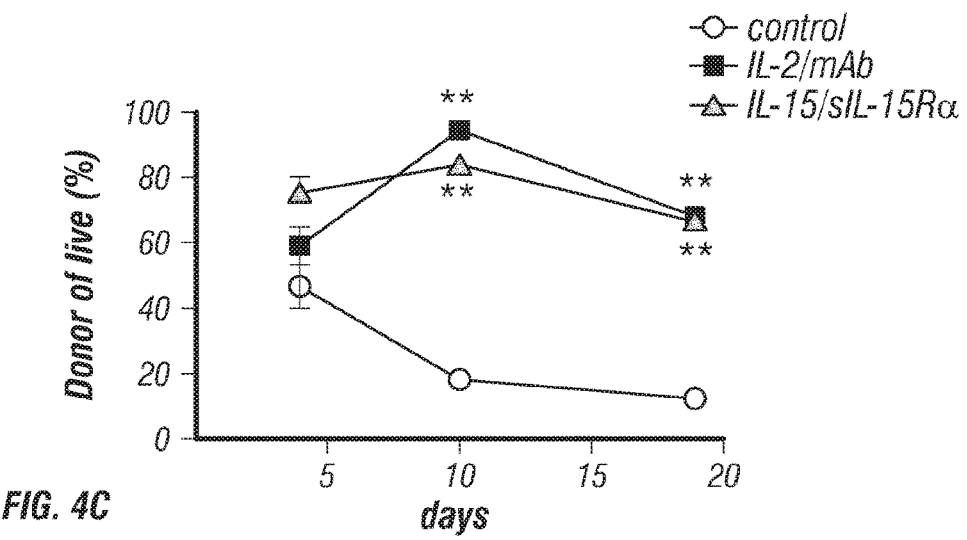
Figure 21A:
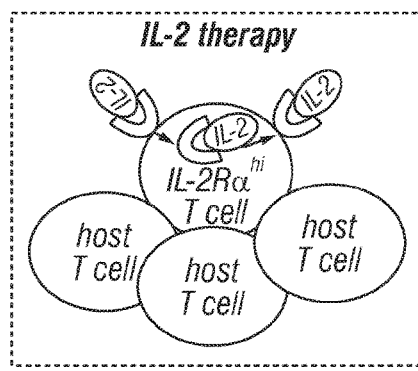
FIGS. 21a-21c—In lymphodepleted mice, IL-15/sIL-15Rα and hIL-2/mAb mediate comparable engraftment of Tc1 effector CD8$_+$ T cells. (a) Diagram depicting the ability of IL-2 to preferentially engage IL-2Rα$^{hi}$ donor T cells, while IL-15 requires removal of host cells for equivalent activity on donor T cells. (b) Mice (n=5/group) were treated without (top) or with (bottom) total body irradiation (TBI, 600 rad) one day prior to adoptive transfer of 10$_7$ pmel-1 Tc1 cells. Then on days 0, 2, 4, and 6, mice were treated with hIL-2/mAb (clone 5355) or hIL-15/sIL-15Rα complexes. Spleens were harvested on day 8. Each triangle represents one mouse and the bar indicates the mean. (**) indicates a significant difference (p<0.001) between control and indicated conditions. Results are representative of 2 independent experiments. (c) A schematic showing the effect of IL-2 of adoptive cell transfer (ACT) therapy with ACT only, ACT plus lymphodepletion and ACT using cells having increased IL-2R activity (IL-2Rα$^{hi}$).
Figure 21A:
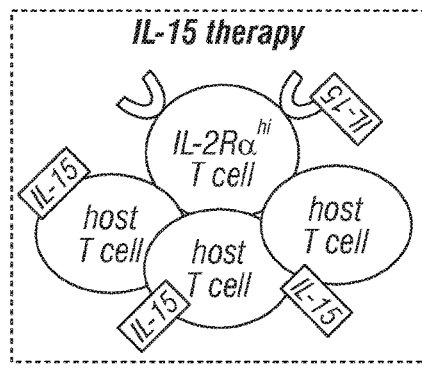
Figure 21A:
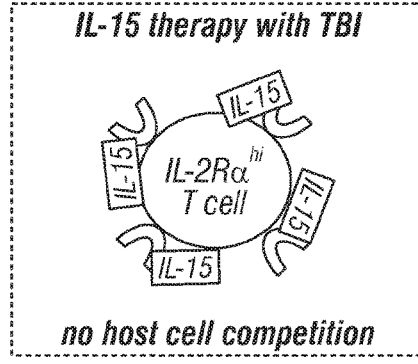
Figure 21B:
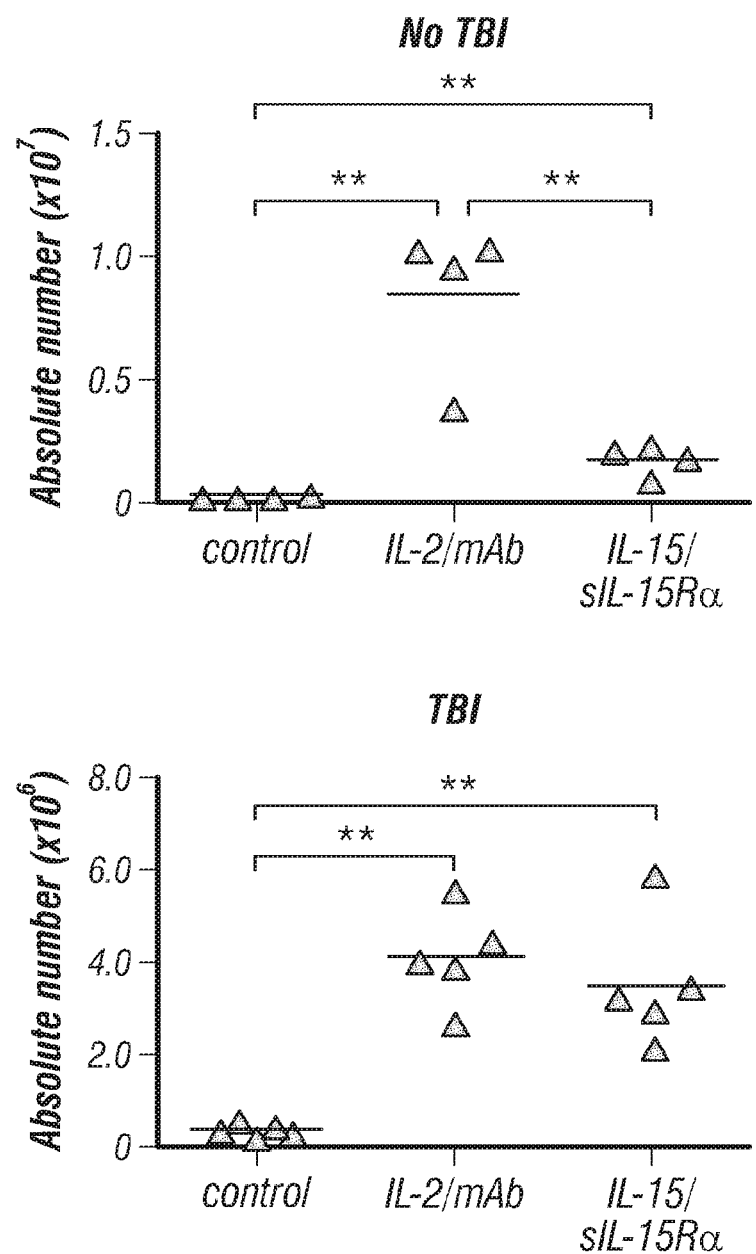
Figure 21C:
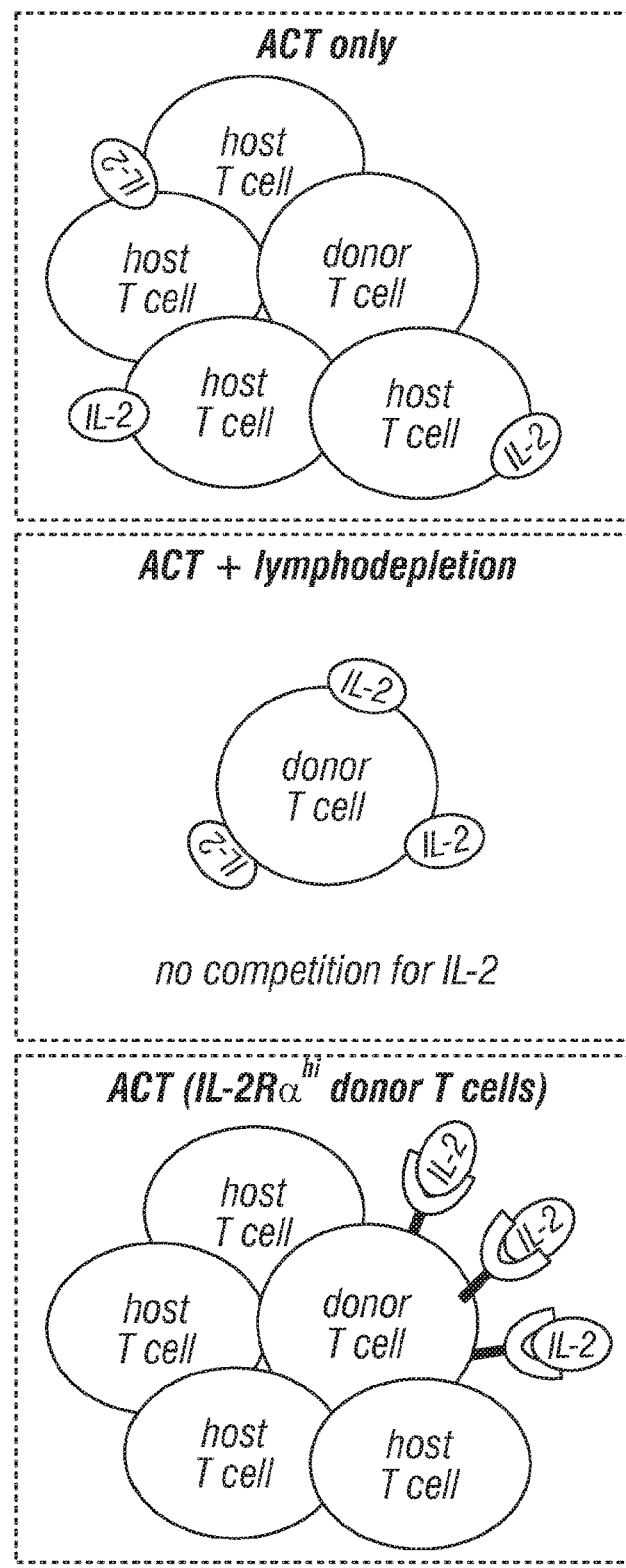
Figure 22:
FIG. 22—An example nucleic acid vector of the embodiments. Shown is a retroviral vector encoding T-cell receptor (TCR) genes (alpha and beta) and an IL-2Rα(CD25) molecule. The TCR could be specific for, as an example, a tumor antigen such as MART-1 or tyrosinase. In this case, the vector could be used to genetically modify T cells, which will then be transferred into a cancer patient. A patient having cells comprising such a vector will be able to respond much more efficiently to IL-2-based therapies.

As an alternative means of assessing the role of IL-2Rα on donor T cells in vivo, the inventors compared the responsiveness of IL-2Rα$^{hi}$ donor T cells to IL-2- and IL-15 therapy with the addition of lymphodepletion to destroy host cells. The inventors predicted that the advantage of IL-2Rα-competent cytokine therapy would be lost in the absence of host IL-2Rβγ+ lymphocytes competing for cytokine (FIG. 21a). Thus, mice were given total body irradiation (600 rad) prior to adoptive transfer of effector Tc1 CD8+ T cells, and then treated for one week with IL-2/mAb and IL-15/sIL-15Rα complexes. Consistent with the prediction, both IL-2 and IL-15 therapy effectively augmented the persistence of donor cells both in the blood and in the spleen, and only in lymphodepleted mice (FIGS. 4c and 21b-c). These results demonstrate a critical role for IL-2Rα on donor T cells in promoting IL-2 responsiveness in a lymphoreplete host environment.

Figure 23:
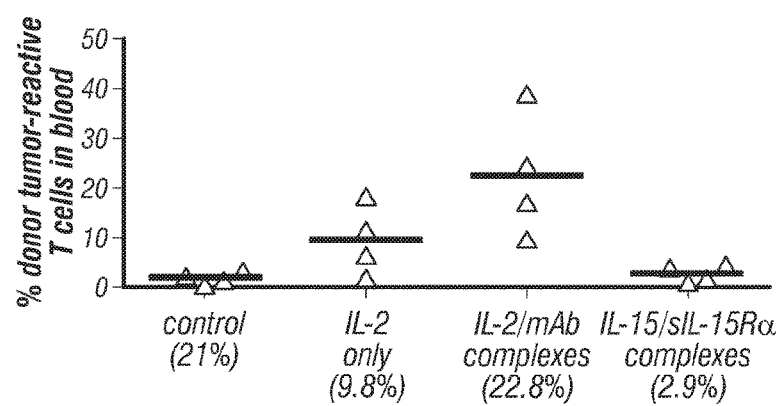
FIG. 23—Low-dose IL-2 leads to preferential expansion of adoptively transferred donor tumor-reactive T cells by engagement of IL-2Rα. B6 mice were injected with 250,000 B16-F1 tumor cells (s.c.). Eight days later, mice were adoptively transferred with 3×10$^6$ tumor-reactive activated T cells (pmel-1) conditioned with IL-12 to induce high levels of IL-2Rα. On the day of adoptive T cell transfer, 2 days later, and 4 days later, mice were treated with hIL-2 (1.5 ug), hIL-2/mAb complexes (1.5 ug hIL-2 and 7.5 ug anti-hIL-2 mAb (MAB602)), or hIL-15/sIL-15Rα-Fc complexes (0.5 ug hIL-15+2.3 ug sIL-15Rα-Fc). On day 6 after adoptive transfer, mice were bled and the frequency of donor T cells (CD8$^+$Thy1.1$^+$) in the peripheral blood was determined. Each triangle represents an individual mouse and the bar indicates the mean. The number in parenthesis and in red indicates the frequency of donor T cells in the blood.

It was also shown that low-dose IL-2 leads to preferential expansion of adoptively transferred donor tumor-reactive T cells by engagement of IL-2Rα (FIG. 23). B6 mice were injected with 250,000 B16-F1 tumor cells (s.c.). Eight days later, mice were adoptively transferred with 3×10$^6$ tumor-reactive activated T cells (pmel-1) conditioned with IL-12 to induce high levels of IL-2Rα. On the day of adoptive T cell transfer, 2 days later, and 4 days later, mice were treated with hIL-2 (1.5 ug), hIL-2/mAb complexes (1.5 ug hIL-2 and 7.5 ug anti-hIL-2 mAb (MAB602)), or hIL-15/sIL-15Rα-Fc complexes (0.5 ug hIL-15+2.3 ug sIL-15Rα-Fc). On day 6 after adoptive transfer, mice were bled and the frequency of donor T cells (CD8+ Thy1.1+) in the peripheral blood was determined.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Amano et al., "A hydrophobic amino acid cluster inserted into the C-terminus of a recycling cell surface receptor functions as an endosomal sorting signal," BBRC, 441: 164-168, 2013.

Boyman et al., "Selective Stimulation of T Cell Subsets with Antibody-Cytokine Immune Complexes," Science, 311: 1924-1927, 2006.

Boyman et al., Selective stimulation of T cell subsets with antibody-cytokine immune complexes. Science 311, 1924-1927, 2006.

Grant and Donaldson, Pathways and mechanisms of endocytic recycling. Nature reviews. Molecular cell biology 10, 597-608, 2009.

Lisiero et al., Enhanced sensitivity to IL-2 signaling regulates the clinical responsiveness of IL-12-primed CD8(+) T cells in a melanoma model. Journal of immunology 186, 5068-5077, 2011.

Liu et al., The alpha chain of the IL-2 receptor determines the species specificity of high-affinity IL-2 binding. Cytokine 8, 613-621, 1996.

Mu et al., EEA1, an early endosome-associated protein. EEA1 is a conserved alpha-helical peripheral membrane protein flanked by cysteine "fingers" and contains a calmodulin-binding IQ motif. J Biol Chem 270, 13503-13511, 1995.

Robb and Greene, Internalization of interleukin 2 is mediated by the beta chain of the high-affinity interleukin 2 receptor. The Journal of experimental medicine 165, 1201-1206, 1987.

Rubinstein et al., "Converting IL-15 to a superagonist by binding to soluble IL-15R{alpha}," Proc Natl Acad Sci USA., 103(24):9166-71, 2006.

Rubinstein et al., Converting IL-15 to a superagonist by binding to soluble IL-15R{alpha}. Proceedings of the National Academy of Sciences of the United States of America 103, 9166-9171, 2006.

Rubinstein et al., Ex vivo interleukin-12-priming during CD8(+) T cell activation dramatically improves adoptive T cell transfer antitumor efficacy in a lymphodepleted host. Journal of the American College of Surgeons 214, 700-707; discussion 707-708, 2012.

Rubinstein et al., IL-7 and IL-15 differentially regulate CD8+ T-cell subsets during contraction of the immune response. Blood 112, 3704-3712, 2008.

Shin et al., "Epigenetic Modifications Induced by Blimp-1 Regulate CD8+ T Cell Memory Progression during Acute Virus Infection," Immunity, 39:661-675, 2013.

Spangler et al., Antibodies to Interleukin-2 Elicit Selective T Cell Subset Potentiation through Distinct Conformational Mechanisms. Immunity 42, 815-825, 2015.

Stoklasek et al., Combined IL-15/IL-15Ralpha immunotherapy maximizes IL-15 activity in vivo. Journal of immunology 177, 6072-6080, 2006.

Takeshita et al., Cloning of the gamma chain of the human IL-2 receptor. Science 257, 379-382, 1992.

Teege et al., Tuning IL-2 signaling by ADP-ribosylation of CD25. Scientific reports 5, 8959, 2015.

Willerford, et al. Interleukin-2 receptor alpha chain regulates the size and content of the peripheral lymphoid compartment. Immunity 3, 521-530, 1995.

What is claimed is:

1. An isolated T-cell comprising a recombinant vector comprising a nucleic acid molecule encoding the IL-2α receptor.

2. The isolated transgenic T-cell of claim 1, wherein the isolated transgenic T-cell is a human T-cell.

3. The isolated transgenic T-cell of claim 1, wherein the T-cell is a T-cell targeted to a cancer cell antigen.

4. The isolated transgenic T-cell of claim 3, wherein the cancer cell antigen is GP240, 5T4, HER1, CD-33, CD-38, VEGFR-1, VEGFR-2, CEA, FGFR3, IGFBP2, IGF-1R, BAFF-R, TACI, APRIL, Fn14, EGFR, ERBB2, ERBB3 CD19, CD20 or mesothelin.

5. The isolated transgenic T-cell of claim 1, wherein the T-cell expresses a chimeric antigen receptor (CAR) or a recombinant T-cell receptor (TCR).

6. The isolated transgenic T-cell of claim 1, wherein the mutation increases surface expression, increases stability or increases ligand binding of the IL-2α receptor polypeptide.

7. The isolated transgenic T-cell of claim 1, comprising the nucleic acid molecule encoding the IL-2α receptor is operably linked to a heterologous promoter.

8. The isolated transgenic T-cell of claim 7, wherein the heterologous promoter is a ligand inducible promoter.

9. The isolated transgenic T-cell of claim 1, wherein the nucleic acid molecule encoding IL-2Rα comprises a mutation that increases the activity of the IL-2Rα.

* * * * *

UNITED STATES PATENT AND TRADEMARK OFFICE
CERTIFICATE OF CORRECTION

PATENT NO.         : 10,377,988 B2
APPLICATION NO.    : 15/533103
DATED              : August 13, 2019
INVENTOR(S)        : Mark Rubinstein and David Cole Page 1 of 1

It is certified that error appears in the above-identified patent and that said Letters Patent is hereby corrected as shown below:

In the Claims

Claim 1, Column 23, Line 29, after "isolated" insert --transgenic--.

Signed and Sealed this
Twenty-second Day of October, 2019

Andrei Iancu
*Director of the United States Patent and Trademark Office*

SEQUENCE LISTING

```
<160> NUMBER OF SEQ ID NOS: 2

<210> SEQ ID NO 1
<211> LENGTH: 9
<212> TYPE: PRT
<213> ORGANISM: Artificial sequence
<220> FEATURE:
<223> OTHER INFORMATION: Synthetic peptide

<400> SEQUENCE: 1

Lys Val Pro Arg Asn Gln Asp Trp Leu
1               5

<210> SEQ ID NO 2
<211> LENGTH: 8
<212> TYPE: PRT
<213> ORGANISM: Artificial sequence
<220> FEATURE:
<223> OTHER INFORMATION: Synthetic peptide

<400> SEQUENCE: 2

Ser Ile Ile Asn Phe Glu Lys Leu
1               5
```